United States Patent
Uchida et al.

(10) Patent No.: US 11,478,408 B2
(45) Date of Patent: *Oct. 25, 2022

(54) TWO-PASTE TYPE DENTAL RESIN-REINFORCED GLASS IONOMER CEMENT COMPOSITION

(71) Applicant: SHOFU INC., Kyoto (JP)

(72) Inventors: Jun Uchida, Kyoto (JP); Tomohiro Kumagai, Kyoto (JP); Ken Hiratsuka, Kyoto (JP)

(73) Assignee: SHOFU INC., Kyoto (JP)

( * ) Notice: Subject to any disclaimer, the term of this patent is extended or adjusted under 35 U.S.C. 154(b) by 127 days.

This patent is subject to a terminal disclaimer.

(21) Appl. No.: 16/829,226

(22) Filed: Mar. 25, 2020

(65) Prior Publication Data

US 2021/0000698 A1    Jan. 7, 2021

(30) Foreign Application Priority Data

| Mar. 26, 2019 | (JP) | JP2019-057535 |
| Mar. 26, 2019 | (JP) | JP2019-057536 |
| Mar. 26, 2019 | (JP) | JP2019-057537 |
| Mar. 26, 2019 | (JP) | JP2019-057538 |
| Mar. 26, 2019 | (JP) | JP2019-057555 |
| Mar. 26, 2019 | (JP) | JP2019-057556 |
| Aug. 19, 2019 | (JP) | JP2019-150038 |
| Sep. 26, 2019 | (JP) | JP2019-175309 |
| Sep. 26, 2019 | (JP) | JP2019-175327 |
| Sep. 26, 2019 | (JP) | JP2019-175336 |
| Sep. 26, 2019 | (JP) | JP2019-175354 |
| Dec. 24, 2019 | (JP) | JP2019-232733 |

(51) Int. Cl.

| *A61K 6/889* | (2020.01) |
| *A61K 6/20* | (2020.01) |
| *A61K 6/833* | (2020.01) |
| *C08F 120/56* | (2006.01) |
| *A61K 6/836* | (2020.01) |
| *A61K 6/62* | (2020.01) |
| *A61K 6/77* | (2020.01) |
| *A61K 6/30* | (2020.01) |
| *A61K 6/40* | (2020.01) |
| *A61K 6/887* | (2020.01) |

(52) U.S. Cl.
CPC ............... *A61K 6/889* (2020.01); *A61K 6/20* (2020.01); *A61K 6/30* (2020.01); *A61K 6/40* (2020.01); *A61K 6/62* (2020.01); *A61K 6/77* (2020.01); *A61K 6/833* (2020.01); *A61K 6/836* (2020.01); *A61K 6/887* (2020.01); *C08F 120/56* (2013.01)

(58) Field of Classification Search
CPC ...................................................... A61K 6/889
See application file for complete search history.

(56) References Cited

U.S. PATENT DOCUMENTS

| 5,154,762 | A | 10/1992 | Mitra et al. | |
| 6,214,101 | B1 | 4/2001 | Nakaseco | |
| 10,736,822 | B2 * | 8/2020 | Amao | C08F 222/385 |
| 2002/0143138 | A1 * | 10/2002 | Moszner | A61K 6/20 528/310 |
| 2006/0247330 | A1 | 11/2006 | Takano et al. | |
| 2014/0039087 | A1 * | 2/2014 | Stelzig | A61K 6/889 523/113 |
| 2017/0296442 | A1 * | 10/2017 | Renn | A61K 6/77 |
| 2018/0296445 | A1 | 10/2018 | Amao et al. | |

FOREIGN PATENT DOCUMENTS

| CA | 2 368 064 | 7/2002 | |
| JP | 11-228327 | 8/1999 | |
| JP | 3288698 | 6/2002 | |
| JP | 4171600 | 10/2008 | |
| WO | WO-2017135186 A1 * | 8/2017 | A61K 6/54 |
| WO | WO-2018143051 A1 * | 8/2018 | A61K 6/00 |

OTHER PUBLICATIONS

Extended European Search Report dated Oct. 7, 2020, in corresponding European Patent Application No. 20165739.2.

* cited by examiner

*Primary Examiner* — Michael F Pepitone
(74) *Attorney, Agent, or Firm* — Wenderoth, Lind & Ponack, L.L.P.

(57) ABSTRACT

An object of the present invention is to provide a two-paste type dental resin-reinforced glass ionomer cement composition which exhibit high surface curability even under wet conditions, which makes difficult for the surface to become cloudy even if moisture comes in contact with at the initial stage of curing, exhibits high mechanical properties, low water absorption expansion and excellent coloring resistance in the set product and is also excellent in storage stability. The two-paste type dental resin-reinforced glass ionomer cement composition of the present invention consists of two pastes, wherein at least one of the two pastes contains (a) acid-reactive glass powder, (b) polymer of acidic group-containing polymerizable monomer, (c) water, (d) hydroxyl group-containing (meth)acrylate-based polymerizable monomer, (e) tri or more functional (meth)acrylamide-based polymerizable monomer, and (f) polymerization initiator, wherein the paste containing the (c) water does not contain at least one of the (a) acid-reactive glass powder and the (b) polymer of acidic group-containing polymerizable monomer.

14 Claims, No Drawings

TWO-PASTE TYPE DENTAL RESIN-REINFORCED GLASS IONOMER CEMENT COMPOSITION

CROSS-REFERENCE TO RELATED APPLICATIONS

This application is based on and claims the benefit of priorities from Japanese Patent Application Serial No. 2019-57535, Japanese Patent Application Serial No. 2019-57536, Japanese Patent Application Serial No. 2019-57537 and Japanese Patent Application Serial No. 2019-57538 (filed on Mar. 26, 2019), Japanese Patent Application Serial No. 2019-150038 (filed on Aug. 19, 2019), Japanese Patent Application Serial No. 2019-175309, Japanese Patent Application Serial No. 2019-175327, Japanese Patent Application Serial No. 2019-175336 and Japanese Patent Application Serial No. 2019-175354 (filed on Sep. 26, 2019), and, Japanese Patent Application Serial No. 2019-232733 (filed on Dec. 24, 2019), the contents of which are hereby incorporated by reference in their entirety.

BACKGROUND OF THE INVENTION

Field of the Invention

The present invention relates to a two-paste type dental resin-reinforced glass ionomer cement composition for filling for repairing a tooth in which a form was partially lost by caries, breakages and the like and a two-paste type dental resin-reinforced glass ionomer cement composition for luting for adhering or bonding a dental prosthesis device to a tooth in which a form was partially lost. More specifically, the present invention relates to a two-paste type dental resin-reinforced glass ionomer cement composition for filling and a two-paste type dental resin-reinforced glass ionomer cement composition for luting which exhibit high surface curability even under wet conditions, which makes it difficult for the surface to become cloudy even if moisture comes in contact with at the initial stage of curing, exhibits high mechanical properties, low water absorption expansion and excellent coloring resistance in the set product and is also excellent in storage stability and mixability.

Description of the Related Art

In a dental practice, in order to restore aesthetically and functionally the tooth in which a form was partially lost by caries, breakages and the like, a direct restoration in which various dental filling materials are filled into the tooth and an indirect restoration in which a dental prosthesis device is adhered or bonded to a tooth by using various dental adhesive/luting material have been performed.

The dental filling material and the dental adhesive/luting material include a dental resin material containing a polymerizable monomer, a filler such as a glass filler, as a main component and a dental glass ionomer cement containing a polycarboxylic acid, water, and acid-reactive glass powder as a main component. Furthermore, a dental resin-reinforced glass ionomer cement composition containing a combination of the components of both a dental resin material and a dental glass ionomer cement (Japanese Patent No. 3288698 B).

Among them, the dental resin-reinforced glass ionomer cement composition has the advantages of both the dental resin material and the dental glass ionomer cement, and has a long-term fluoride sustained release ability, and transparency that exceeds conventional dental glass ionomer cements. Furthermore, since the curability of the polymerizable monomer is imparted by radical polymerization, the cloudiness of the surface due to the contact of water at the initial stage of setting, which was a problem of the conventional dental glass ionomer cement that is set only by acid-base reaction, is relatively unlikely to occur.

Although the initial dental resin-reinforced glass ionomer cement composition consists of a powder material and a liquid material and is used by mixing to start curing reaction, a dental resin-reinforced glass ionomer cement composition consisting of two paste in order to improve the mixing property to stably exhibit characteristics has been proposed (Japanese Unexamined Patent Application Publication No. H11-228327 A).

However, since the two-paste type dental resin-reinforced glass ionomer cement composition contains water that does not contribute to polymerization and curing, the curability of the polymerizable monomer due to radical polymerization is low, and the curability is still insufficient on the surface that is further affected by polymerization inhibition by oxygen. Therefore, the set product of the two-paste type dental resin-reinforced glass ionomer cement composition has been easily colored. Further, since the two-paste type dental resin-reinforced glass ionomer cement composition contains a hydrophilic polymerizable monomer as a main component in consideration of the compatibility with water contained in the composition, the set product has a large water absorption amount which is associated with the above-mentioned low polymerization-curability, therefore the water absorption expansion tended to increase. Furthermore, further improvement has been demanded for the cloudiness of the surface due to the contact of moisture at the initial stage of curing.

Further, when the paste constituting the two-paste type dental resin-reinforced glass ionomer cement composition contains a polycarboxylic acid, water and a polymerizable monomer simultaneously, the polymerizable monomer is hydrolyzed to cause various problems. Specifically, when a (meth)acrylate-based polymerizable monomer most used in dental materials is used as a polymerizable monomer, the ester bond of the (meth)acrylate group is hydrolyzed and methacrylic acid or acrylic acid, which has high polymerization activity, is generated. Therefore, there is a problem in storage stability such that the paste gels during storage and the mechanical properties of the set product deteriorate. This tendency is particularly remarkable in the paste further containing a polymerizable monomer having an acidic group.

On the other hand, a technique of applying a (meth)acrylamide-based polymerizable monomer that is hard to hydrolysis to various dental materials is disclosed.

For example, Japanese Patent No. 4171600 B discloses a technique for obtaining various dental materials which is hard to hydrolysis and has excellent storage stability even in the presence of an acidic group-containing polymerizable monomer, by applying a di to penta functional (meth)acrylamide-based polymerizable monomer. However, the effects obtained in case that the (meth)acrylamide-based polymerizable monomer is applied to a two-paste type dental resin-reinforced glass ionomer cement composition are not suggested in this patent document, except for improvement in storage stability. In addition, there is no indication about the structure or the number of functional groups of the (meth)acrylamide-based polymerizable monomer suitable for application to two-paste type dental resin-reinforced glass ionomer cement composition.

SUMMARY OF THE INVENTION

Technical Problem

In the conventional two-paste type dental resin-reinforced glass ionomer cements, the surface of the set product is less likely to become cloudy due to contact with moisture at the initial stage of setting, by having curability due to radical polymerization. However, it cannot be said that it has been sufficiently improved, and further improvement in surface curability has been demanded. In addition, since the water absorption expansion of the set product is large, the lift of the restoration causes the patient to feel uncomfortable, and in some cases, there is a risk that the dental occlusion with the pairing tooth deteriorates. Furthermore, the property of being easily colored has not been improved yet, and the repair site could not be aesthetically maintained for a long period of time. Therefore, an object of the present invention is to provide a two-paste type dental resin-reinforced glass ionomer cement composition which maintains the excellent properties of the conventional two-paste type dental resin-reinforced glass ionomer cement composition (such as mixability and fluoride sustained releasability), further improves the surface curability, shows a small water absorption expansion and excellent coloring resistance, further stably expresses various properties for a long period and is excellent in storage stability.

Solution to Problem

As a result of intensive studies to solve the above problems, the present inventors have found that the curability of the polymerizable monomer in the coexistence of water is dramatically improved, therefore an excellent surface curability is exhibited, the surface of the set product is less likely to be colored, and the water-absorption expansion is reduced, by simultaneously compounding a tri or more functional (meth)acrylamide-based polymerizable monomer together with a (meth)acrylate-based polymerizable monomer having a hydroxyl group as a polymerizable monomer in the basic components of conventional two-paste type dental resin-reinforced glass ionomer cements, that is, an acid-reactive glass powder represented by fluoroaluminosilicate glass powder, a polymer of an acidic group-containing polymerizable monomer represented by polyacrylic acid, water, a polymerizable monomer, and a polymerization initiator. Further, the present inventors have found that by compounding a tri or more functional (meth)acrylamide-based polymerizable monomer, other polymerizable monomers are less susceptible to hydrolysis even under acidic conditions, and the storage stability of the paste is improved. Further, the present inventors have found that the surface curability and the coloring resistance are further improved and the water absorption expansion is further reduced in case of containing both a mono functional (meth)acrylate-based polymerization monomer that has a hydroxyl group and a bi to tetra functional (meth)acrylate-based polymerizable monomer that has hydroxyl group as the (meth)acrylate-based polymerizable monomer having a hydroxyl group in a specific ratio and/or in case of compounding a tetra or more functional (meth)acrylamide-based polymerizable monomer as the tri or more functional (meth)acrylamide-based polymerizable monomer, and the present invention has been completed.

That is, the above problems are solved by the two-paste type dental resin-reinforced glass ionomer cement composition of the present invention consisting of two pastes, wherein at least one of the two pastes contains (a) acid-reactive glass powder, (b) polymer of acidic group-containing polymerizable monomer, (c) water, (d) hydroxyl group-containing (meth)acrylate-based polymerizable monomer, (e) tri or more functional (meth)acrylamide-based polymerizable monomer, and (f) polymerization initiator, wherein the paste containing the (c) water does not contain at least one of the (a) acid-reactive glass powder and the (b) polymer of acidic group-containing polymerizable monomer.

It is preferable in the two-paste type dental resin-reinforced glass ionomer cement composition of the present invention that at least one of the two pastes further contains (g) acidic group-containing polymerizable monomer, wherein the paste containing the (c) water does not contain at least one of the (a) acid-reactive glass powder and the (g) acidic group-containing polymerizable monomer.

It is preferable that the (b) polymer of acidic group-containing polymerizable monomer is a polymer of an α,β-unsaturated carboxylic acid.

It is preferable that the (d) hydroxyl group-containing (meth)acrylate-based polymerizable monomer contains both a mono functional (meth)acrylate-based polymerization monomer that has a hydroxyl group and a bi to tetra functional (meth)acrylate-based polymerizable monomer that has hydroxyl group and the compounding ratio of the mono functional (meth)acrylate-based polymerization monomer that has a hydroxyl group and the bi to tetra functional (meth)acrylate-based polymerizable monomer that has hydroxyl group is 1:2 to 4:1 by weight.

It is preferable that the (e) tri or more functional (meth)acrylamide-based polymerizable monomer is a tetra or more functional (meth)acrylamide-based polymerizable monomer.

It is preferable that the (e) tri or more functional (meth)acrylamide-based polymerizable monomer is a compound represented by formula (1):

[Chemical Formula 1]

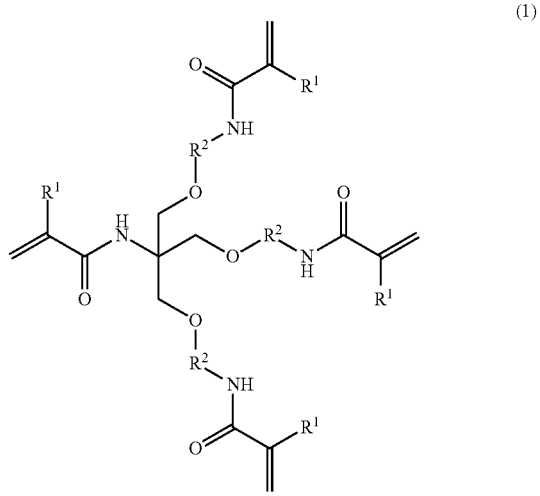

(1)

(In formula, $R^1$ represents a hydrogen atom or a methyl group and $R^1$s may be the same or different from each other, and $R^2$ represents a linear or branched alkylene group having 2 to 6 carbon atoms which may have a substituent and $R^2$s may be the same or different from each other.)

It is preferable that all $R^1$s in the formula (1) are hydrogen atom.

It is preferable that the (e) tri or more functional (meth)acrylamide-based polymerizable monomer is a compound represented by formula (2):

[Chemical Formula 2]

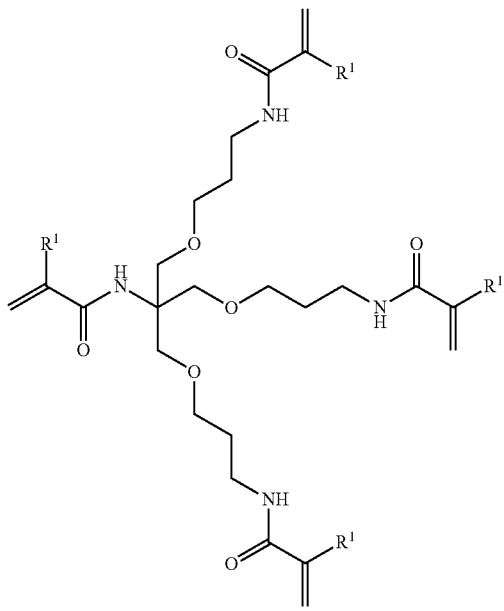

(2)

(In formula, $R^1$ represents a hydrogen atom or a methyl group and $R^1$s may be the same or different from each other.)

It is preferable that all $R^1$s in the formula (2) are hydrogen atom.

Advantageous Effects of Invention

Since the two-paste type dental resin-reinforced glass ionomer cement composition of the present invention can be easily mixed, a difference in a degree of mixing depending on the operator is unlikely generated and various characteristics can be stably expressed. Further, since high surface curability is exhibited even under wet conditions, even in a clinical case where it is difficult to remove moisture, clouding of the surface due to poor curing hardly occurs. Furthermore, since the set product exhibits excellent mechanical properties and coloring resistance, the initial restoration state can be maintained for a long period of time, and since the water absorption expansion is small, discomfort at the time of occlusion due to floating of the restoration is less likely to occur. In addition to these, since these are also excellent in storage stability, their characteristics can be stably exhibited for a long period of time.

DETAILED DESCRIPTION OF THE PREFERRED EMBODIMENTS

The present invention will be described in further detail below.

The two-paste type dental resin-reinforced glass ionomer cement composition of the present invention consisting of two pastes, wherein at least one of the two pastes contains (a) acid-reactive glass powder, (b) polymer of acidic group-containing polymerizable monomer, (c) water, (d) hydroxyl group-containing (meth)acrylate-based polymerizable monomer, (e) tri or more functional (meth)acrylamide-based polymerizable monomer, and (f) polymerization initiator, wherein the paste containing the (c) water does not contain at least one of the (a) acid-reactive glass powder and the (b) polymer of acidic group-containing polymerizable monomer.

In the present specification, the term "(meth)acrylate" inclusively refers to both acrylate and methacrylate, the term "(meth)acryloyl" inclusively refers to both acryloyl and methacryloyl, and the term "(meth)acrylamide" inclusively refers to both acrylamide and methacrylamide.

The (a) acid-reactive glass powder that can be used in the two-paste type dental resin-reinforced glass ionomer cement composition of the present invention contains an acid-reactive element and fluorine. Because the acid reactive glass powder includes an acid reactive element, the acid-base reaction of the (a) acid reactive glass powder with the acid group contained in the (b) polymer of an acid group-containing polymerizable monomer described later progresses in the presence of water. Specific examples of an acid reactive element include sodium, potassium, calcium, strontium, barium, lanthanum, aluminum and zinc, but are not limited thereto. One or two or more kinds of these acid reactive element may be contained and a content thereof is not particularly limited.

Further, it is preferable that the acid reactive glass powder includes an X-ray impermeable element in order to impart X-ray contrast property to the two-paste type dental resin-reinforced glass ionomer cement composition of the present invention. Specific examples of an X-ray impermeable element include strontium, lanthanum, zirconium, titanium, yttrium, ytterbium, tantalum, tin, tellurium, tungsten and bismuth, but are not limited thereto. In addition, other element contained in the acid reactive glass powder is not particularly limited and the acid reactive glass powder in the present invention may include various elements.

Specific examples of the acid reactive glass powder include aluminosilicate glass, borosilicate glass, aluminoborate glass, boro aluminosilicate glass, phosphate glass, borate glass, and silica glass which contains the above described acid reactive element, fluorine element and X-ray impermeable element, but are not limited thereto.

Further, a particle shape of the acid reactive glass powder is not particularly limited, but arbitral particle shapes such as spherical, needle-like, plate-like, ground-like, and scaly-shape may be used without any limitation. These acid reactive glass powder may be used alone or in combination of two or more thereof.

A preparing method of the acid reactive glass powder is not particularly limited, but an acid reactive glass powder prepared by any process such as a melting method, a vapor phase method and a sol-gel method may be used without any problem. Among them, the acid reactive glass powder prepared by a melting method or a sol-gel method which can easily control a kind of element contained in the acid-reactive glass powder and the content thereof is preferably used.

As the acid-reactive glass powder, fillers which are generally sold may be used without processing such as grinding, but it is possible to adjust to a desired average particle diameter by grinding appropriately according to the application or purpose and usage of the two-paste type dental resin-reinforced glass ionomer cement composition of the present invention. A grinding method is not particularly limited, but an acid-reactive glass powder obtained by grinding which use any of wet or dry grinding methods may be used. Specifically, the acid reactive glass powder may be ground by a high speed rotating mill such as a hammer mill and a turbo-mill, a container driving medium mill such as a ball mill and a vibration mill, a medium stirring mill such as a sand grinder and attritor, and a jet mill and the like.

For example, when the two-paste type dental resin-reinforced glass ionomer cement composition of the present invention is used as a material for filling or abutment building, because high mechanical strength is required, the acid-reactive glass powder has preferably an average particle diameter in the range of 0.01 to 30.0 μm, more preferably in the range of 0.01 to 10.0 μm.

In addition, when the two-paste type dental resin-reinforced glass ionomer cement composition of the present invention is used as a material for luting, because a thin film thickness is required, the acid-reactive glass powder has preferably an average particle diameter in the range of 0.01 to 10.0 μm, more preferably in the range of 0.01 to 5.0 μm.

When the average particle diameter of the acid-reactive glass powder is less than 0.01 μm, the surface area of the acid-reactive glass powder increases and it becomes impossible to contain the acid-reactive glass powder in a large amount into the composition, therefore there is a risk that deterioration in mechanical characteristics may be caused. In addition, there is a case that the stickiness of the mixed product may increase and the operability may deteriorate.

In case of using as a material for filling or abutment building, when the average particle diameter of the acid-reactive glass powder exceeds 30.0 μm, the surface of the material after polishing becomes rough, therefore coloring may be caused. Further, in case of using as a material for luting, when the average particle diameter of the acid-reactive glass powder exceeds 10.0 μm, because the film thickness becomes thick, the attached dental prosthesis device is lifted and therefore there is a risk that the intended fit cannot be obtained.

The acid reactive glass powder may be treated with various surface treatments, heat treatment, aggregating treatment in a liquid phase or a vapor phase, microcapsulation in which the surface is enclosed with an organic substance, grafting in which a surface is functionalized with an organic substance and the like to such a range that the acid-base reaction of the acid reactive glass powder with the acid group contained in the (b) polymer of an acid group-containing polymerizable monomer described later is not adversely affected, in order to adjust operability, curing characteristics, mechanical characteristics and the like of the two-paste type dental resin-reinforced glass ionomer cement composition of the present invention. These treatments can be performed alone or in a combination of a few kinds, with no problems. Among them, the surface treatment and heat treatment are preferable because it is easy to control various characteristics and those are superior in productivity.

Specific examples of the surface treating method of the acid reactive glass powder include washing with acid such as phosphoric acid or acetic acid, surface treatment with acidity compound such as tartaric acid or polycarboxylic acid, surface treatment with fluoride such as aluminum fluoride and surface treatment with silane compound such as γ-methacryloyloxypropyltrimethoxysilane or tetramethoxy silane. The surface treating method which can be used in the present invention is not limited the above described method and these surface treating methods can be used alone or in a combination thereof.

Specific examples of the heat treating method of the acid reactive glass powder include a treating method which includes heating for a range of 1 to 72 hours within a range of 100° C. to 800° C. using electric furnace. The heat treating method which can be used in the present invention is not limited the above described method and any method of uni-temperature and multi-stage temperature can be used as the heat treating method without any problem.

Any polymer can be used as the (b) polymer of acidic group-containing polymerizable monomer which can be used as the two-paste type dental resin-reinforced glass ionomer cement composition of the present invention as long as it is a polymer of a polymerizable monomer having at least one or more an acid group in a molecule, without any limitation.

As the acidic group-containing polymerizable monomers which may be used for obtaining the polymer of an acid group-containing polymerizable monomer, any acidic group-containing polymerizable monomers may be used regardless of the type of acidic group. In addition, any acidic group-containing polymerizable monomers may be used regardless of the number or the type of radical polymerizable unsaturated groups (monofunctional groups or multifunctional) of the acidic group-containing polymerizable monomer.

Specific examples of the acidic group of the acidic group-containing polymerizable monomer are not limited to, but include a phosphoryl group, a pyrophosphoryl group, a phosphonyl group, a carboxyl group, a sulfonyl group, and a thiophosphoric acid group, but are not limited to. In the two-paste type dental resin-reinforced glass ionomer cement composition of the present invention, it is preferable that other acidic group-containing polymerizable monomer other than the acidic group-containing polymerizable monomer including a phosphoryl group, a pyrophosphoryl group, a phosphonyl group, a carboxyl group, a sulfonyl group, and/or a thiophosphoric acid group.

Specific examples of the unsaturated polymerizable group of the acidic group-containing polymerizable monomer are not limited to, but include a (meth) acryloyl group, a (meth) acrylamide group, a styryl group, a vinyl group, and an aryl group. Among these unsaturated groups, a (meth) acryloyl group and a (meth) acrylamide group are preferable and a (meth) acryloyl group is more preferable.

Further, these acidic group-containing polymerizable monomers may contain together other functional group such as an alkyl group, halogen, an amino group, a glycidyl group and a hydroxy group in a molecule.

Specific examples of an acidic group-containing polymerizable monomers which may be used for obtaining the polymer of an acid group-containing polymerizable monomer and has a (meth) acryloyl group as an unsaturated group, are specifically listed below.

Specific examples of an acidic group-containing polymerizable monomer which has a phosphoryl group are not limited to, but include (meth)acryloyloxymethyl dihydrogen phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-

(meth)acryloyloxyeicosyl dihydrogen phosphate, bis [2-(meth) acryloyloxyethyl] hydrogensphosphate, bis [3-(meth) acryloyloxypropyl]hydrogen phosphate, bis [4-(meth) acryloyloxybutyl] hydrogen phosphate, bis [16-(meta) acryloyloxyhexyl] hydrogen phosphate, bis [8-(meth) acryloyloxyoctyl] hydrogen phosphate, bis [9-(meth) acryloyloxynonyl] hydrogen phosphate, bis [10-(meth) acryloyloxydecyl] hydrogen phosphate, 1,3-di(meth)acryloyloxypropyl-2-dihydrogenphosphate, 2-(meth) acryloyloxyethylphenyl hydrogen phosphate, and 2-(meth) acryloyloxyethyl 2'-bromoethyl hydrogen phosphate.

Specific examples of an acidic group-containing polymerizable monomer which has a pyrophosphoryl group are not limited to, but include, bis [2-(meth) acryloyloxyethyl] pyrophosphate, bis [3-(meth) acryloyloxypropyl] pyrophosphate, bis [4-(meth) acryloyloxybutyl] pyrophosphate, bis [5-(meth) acryloyloxypentyl] pyrophosphate, bis [6-(meth) acryloyloxyhexyl] pyrophosphate, bis [7-(meth) acryloyloxyheptyl] pyrophosphate, bis [8-(meth) acryloyloxyoctyl] pyrophosphate, bis [9-(meth) acryloyloxynonyl] pyrophosphate, bis [10-(meth) acryloyloxydecyl] pyrophosphate, bis [12-(meth) acryloyloxydodecyl] pyrophosphate, tris [2-(meth) acryloyloxyethyl] pyrophosphate and tetra [2-(meth) acryloyloxyethyl] pyrophosphate.

Specific examples of an acidic group-containing polymerizable monomer which has a phosphonyl group are not limited to, but include 5-(meth) acryloyloxypentyl-3-phosphonopropionate, 6-(meth) acryloyloxyhexyl-3-phosphonopropionate, 10-(meth) acryloyloxydecyl-3-phosphonopropionate, 6-(meth) acryloyloxyhexyl-3-phosphonoacetate, 10-(meth) acryloyloxydecyl-3-phosphonoacetate, and (meth) acryloyloxyethl phenyphosphonoacetate.

Specific examples of an acidic group-containing polymerizable monomer which has a carboxyl group are not limited to, but include (meth) acrylic acid, 2-chloro acrylic acid, 3-chloro(meth)acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth) acryloyloxyethylpyromellitic acid, 6-(meth) acryloyloxynaphthalene-1,2,6-tricarboxylic acid, 1-buten-1,2,4-tricarboxylic acid, 3-buten-1,2,3-tricarboxylic acid, N-(meth) acryloyl-p-aminobenzoic acid, N-(meth) acryloyl-5-amino salicylic acid, 4-(meth) acryloyloxyethyltrimellitic acid and anhydride thereof, 4-(meth) acryloyloxybutyltrimellitic acid and anhydride thereof, 2-(meth) acryloyloxybenzoic acid, β-(meth) acryloyloxyethyl hydrogen succinate, β-(meth) acryloyloxyethyl hydrogen maleate, 11-(meth) acryloyloxy-1,1-undecanedicarboxylic acid, p-vinylbenzoic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid and anhydride thereof, 5-(meth) acryloylaminopentylcarboxylic acid, 6-(meth) acryloyloxy-1,1-hexanedicarboxylic acid, 8-(meth) acryloyloxy-1,1-octanedicarboxylic acid, 10-(meth) acryloyloxy-1,1-decanedicarboxylic acid, and 11-(meth) acryloyloxy-1,1-undecanedicarboxylic acid.

Specific examples of an acidic group-containing polymerizable monomer which has a sulfonate group are not limited to, but include 2-(meth) acrylamido-2-methylpropanesulfonic acid, styrene sulfonic acid, 2-sulfoethyl (meth) acrylate, 4-(meth) acryloyloxy benzene sulfonic acid, and 3-(meth) acryloyloxy propanesulfonic acid.

Specific examples of an acidic group-containing polymerizable monomer which has a thiophosphoric acid group are not limited to, but include, 2-(meth) acryloyloxyethyl dihydrogenthiophosphate, 3-(meth) acryloyloxypropyl dihydrogenthiophosphate, 4-(meth) acryloyloxybutyl dihydrogenthiophosphate, 5-(meth) acryloyloxypentyl dihydrogenthiophosphate, 6-(meth) acryloyloxyhexyl dihydrogenthiophosphate, 7-(meth) acryloyloxyheptyl dihydrogenthiophosphate, 8-(meth) acryloyloxyoctyl dihydrogenthiophosphate, 9-(meth) acryloyloxynonyl dihydrogenthiophosphate, 10-(meth) acryloyloxydecyl dihydrogenthiophosphate.

These acidic group-containing polymerizable monomers can be used not only singly but also in combinations of a plurality thereof for synthesize a polymer of the acidic group-containing polymerizable monomer, without any problem. In addition, the polymer of the acidic group-containing polymerizable monomer may be synthesized by copolymerizing an acidic group-containing polymerizable monomer containing one or more acidic group in a molecule and a polymerizable monomer containing no acidic group, without any problem.

It is preferable to use an α,β-unsaturated carboxylic acid based acidic group-containing polymerizable monomers among these acidic group-containing polymerizable monomers. The α,β-unsaturated carboxylic acid based acidic group-containing polymerizable monomer which can be used in this case is not particularly limited and may be used regardless of the number of carboxylic groups in the molecule or the existence of a carboxylic anhydride group or other substituents. In the two-paste type dental resin-reinforced glass ionomer cement composition of the present invention, it is preferable that a polymer of acidic group-containing polymerizable monomer other than α,β-unsaturated carboxylic acid based acidic group-containing polymerizable monomer is not contained.

Specific examples of an α,β-unsaturated carboxylic acid based acidic group-containing polymerizable monomer are not limited to, but include (meth) acrylic acid, 2-chloro acrylic acid, 3-chloro (meth) acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, tiglic acid, 1-buten-1,2,4-tricarboxylic acid, and 3-buten-1,2,3-tricarboxylic acid.

The method of polymerizing various polymerizable monomers is not particularly limited, and a polymer polymerized by any methods such as solution polymerization, suspension polymerization, emulsion polymerization or the like, may be used without any limitation. In addition, a polymerization initiator and a chain transfer agent which can be used at the time of synthesis of a polymer may be appropriately selected in order to obtain a desired polymer. The polymer of an acid group-containing polymerizable monomer obtained by such way can be used alone, or in a combination of a few kinds.

The obtained polymer of the acidic group-containing polymerizable monomer may be used after neutralization reaction of a part of the acidic group thereof by using an alkali metal hydroxide such as sodium hydroxide, potassium hydroxide and lithium hydroxide, an alkali metal carbonate such as sodium carbonate, potassium carbonate and lithium carbonate, and a bicarbonate of an alkali metal such as sodium hydrogen carbonate, potassium hydrogen carbonate, lithium hydrogen carbonate or the like, for the purpose of adjusting the operation surplus time and setting time, or for the purpose of improving storage stability. The compound used for this neutralization is not limited to these, and there is no problem even if the compound may be used alone or in combination of several kinds.

Furthermore, there is no problem even if the polymer of the acidic group-containing polymerizable monomer has a radical polymerizable unsaturated group. However, the polymer of the acidic group-containing polymerizable monomer having an unsaturated group has a relatively low solubility in later discussed (c) water, and there is a tendency that its compounding amount is low, therefore, there is a case that the mechanical property of the set product may be deteriorated. Thus, it is more preferable that the polymer of the acidic group-containing polymerizable monomer does not have an unsaturated group.

It is preferable to use a polymer of an acid group-containing polymerizable monomer synthesized from only acrylic acid as a starting material (poly acrylic acid) or a copolymer of an acid group-containing polymerizable monomer synthesized from two or more kinds of starting materials such as acrylic acid and maleic acid, acrylic acid and maleic anhydride, acrylic acid and itaconic acid, and acrylic acid and 3-butene-1,2,3-tricarboxylic acid.

A weight average molecular weight of the polymer of an acid group-containing polymerizable monomer is not limited particular, but preferably is in a rage of 10,000 to 500,000, more preferably in a rage of 20,000 to 300,000 and further preferably in a rage of 20,000 to 250,000. When a weight average molecular weight of the polymer of an acid group-containing polymerizable monomer is less than 10,000, the mechanical characteristic of a set product may tend to decrease too much to cause problem in durability of the set product. On the other hand, when a weight average molecular weight of the acid group-containing polymerizable monomer is more than 500,000, stickiness of the mixture in mixing the two-paste type dental resin-reinforced glass ionomer cement composition may increase and there may be a problem in operability.

Any water can be used as the (c) water that can be used in the two-paste type dental resin-reinforced glass ionomer cement composition of the present invention as long as it does not contain impurities adversely affecting on the curability and mechanical characteristics of the two-paste type dental resin-reinforced glass ionomer cement composition without any limitation. Specifically, it is preferably to use distilled water, purified water or ion-exchanged water. In the present invention, it is preferable that the (b) polymer of acidic group-containing polymerizable monomer is contained in the paste containing the (c) water.

Any polymerizable monomer can be used as the (d) hydroxyl group-containing (meth)acrylate-based polymerizable monomer which can be used in the two-paste type dental resin-reinforced glass ionomer cement composition of the present invention as long as the monomer has at least one or more hydroxyl group in a molecule and at least one or more (meth)acrylate group as a radical polymerizable unsaturated group in a molecule.

Specific examples of the hydroxyl group-containing (meth)acrylate-based polymerizable monomer include a monofunctional (meth)acrylate-based polymerizable monomer such as 2-hydroxyethyl (meth)acrylate (2-HEMA), 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, 2,3-dihydroxypropyl (meth)acrylate, glycerin mono(meth)acrylate, erythritol mono(meth)acrylate, and an addition product of phenols and glycidyl (meth)acrylate, for example, 2-hydroxy-3-phenoxypropyl (meth)acrylate and 2-hydroxy-3-naphthoxypropyl (meth)acrylate, and a polyfunctional (meth)acrylate-based polymerizable monomers such as 2-hydroxypropyl-1,3-di(meth)acrylate (CDMA), 3-hydroxypropyl-1,2-di(meth)acrylate, bisphenol A diglycidyl (meth)acrylate (Bis-GMA), and 2-hydroxy-3-acryloyloxypropyl methacrylate (GDA). Further, a polyfunctional (meth)acrylate-based polymerizable monomer in which two of more hydroxyl groups of sugar alcohols (erythritol, arabinitol, xylitol, ribitol, iditol, galactitol, sorbitol, mannitol, etc.), monosaccharides (arabinose, xylose, mannose, galactose, fructose, etc.), disaccharides (sucrose, maltose, lactose, trehalose, etc.) and a trisaccharide (maltotriose, raffinose, etc.) are substituted with a substituent having a polymerizable unsaturated group can also be preferably used, but is not limited thereto.

Among them, 2-hydroxyethyl (meth)acrylate, 2-hydroxypropyl (meth)acrylate, 2,3-dihydroxypropyl (meth)acrylate, bisphenol A diglycidyl (meth)acrylate (Bis-GMA), 2-hydroxypropyl-1,3-di(meth)acrylate (GDMA), and 2-hydroxy-3-acryloyloxypropyl methacrylate (GDA) are particularly preferred. Two or more kinds of these (meth)acrylate-based polymerizable monomers having a hydroxyl group may be appropriately used in combination, if desired. In the two-paste type dental resin-reinforced glass ionomer cement composition of the present invention, it is preferable that hydroxyl group-containing (meth)acrylate-based polymerizable monomer other than 2-hydroxyethyl (meth)acrylate, 2-hydroxypropyl (meth)acrylate, 2,3-dihydroxypropyl (meth)acrylate, bisphenol A diglycidyl (meth)acrylate (Bis-GMA), 2-hydroxypropyl-1,3-di(meth)acrylate (GDMA), and 2-hydroxy-3-acryloyloxypropyl methacrylate (GDA) is not contained.

In the two-paste type dental resin-reinforced glass ionomer cement composition of the present invention, it is preferable that the hydroxyl group-containing (meth)acrylate-based polymerizable monomer contains both a mono functional (meth)acrylate-based polymerization monomer that has a hydroxyl group and a bi to tetra functional (meth)acrylate-based polymerizable monomer that has hydroxyl group and the compounding ratio of the mono functional (meth)acrylate-based polymerization monomer that has a hydroxyl group and the bi to tetra functional (meth)acrylate-based polymerizable monomer that has hydroxyl group is 1:2 to 4:1 by weight. By using such a combination and compounding ratio of the (meth)acrylate-based polymerizable monomer having a hydroxyl group, since the (b) polymer of acidic group-containing polymerizable monomer, the (c) water, and the later discussed (e) tri or more functional (meth)acrylamide-based compound are easily and uniformly compatible, the mechanical properties and transparency after curing can be improved. Furthermore, it is more preferable that the bi to tetra functional (meth)acrylate-based polymerizable monomer that has hydroxyl group is a bifunctional (meth)acrylate-based polymerizable monomer having a hydroxyl group.

As the (e) tri or more functional (meth)acrylamide-based polymerizable monomer which can be used in the two-paste type dental adhesive composition of the present invention, any polymerizable monomer as long as the polymerizable monomer contains three or more (meth)acrylamide groups in the molecule can be used without any limitation. It is preferable that the tri or more functional (meth)acrylamide-based polymerizable monomer does not have an acidic group and/or a hydroxyl group because the effect of improving the surface curability and the coloring resistance and reducing the water absorption expansion is easily obtained.

Specific examples of the tri or more functional (meth)acrylamide-based polymerizable monomer include those represented by following formula (1) and formula (3). In the two-paste type dental resin-reinforced glass ionomer cement composition of the present invention, it is preferable that tri or more functional (meth)acrylamide-based polymerizable monomer other than the tri or more functional (meth)acrylamide-based polymerizable monomer include those represented by following formula (1) and formula (3) is not contained.

[Chemical Formula 3]

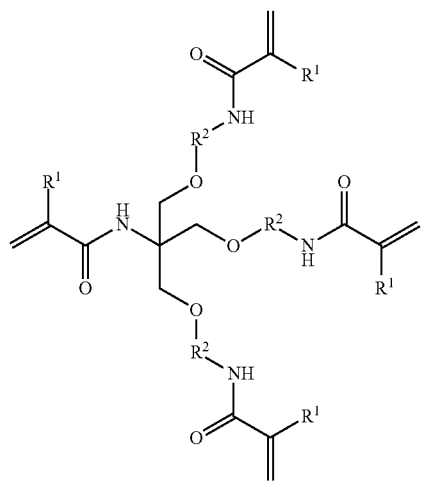

(1)

(In formula, $R^1$ represents a hydrogen atom or a methyl group and $R^1$s may be the same or different from each other, and $R^2$ represents a linear or branched alkylene group having 2 to 6 carbon atoms which may have a substituent and $R^2$s may be the same or different from each other.)

[Chemical Formula 4]

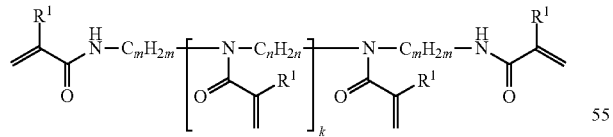

(3)

(In formula, $R^1$ represents a hydrogen atom or a methyl group. The "m" represents an integer of 2 to 4. The "n" represents an integer of 2 to 4. The "k" represents an integer of 0 or 1. A plurality of $R^1$s and the "m"s may be the same or different from each other.)

More specific examples of the tri or more functional (meth)acrylamide-based polymerizable monomer include those represented by following formula (2) and formulas (4) to (7).

[Chemical Formula 5]

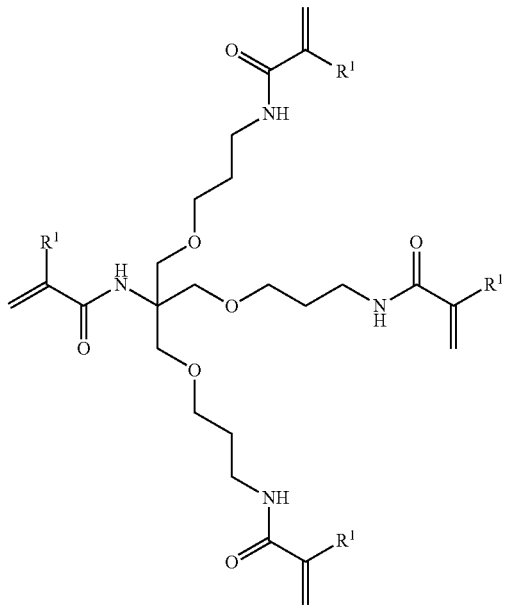

(2)

(In formula, $R^1$ represents a hydrogen atom or a methyl group and $R^1$s may be the same or different from each other.)

[Chemical Formula 6]

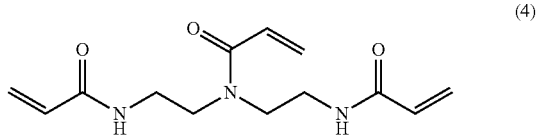

(4)

[Chemical Formula 7]

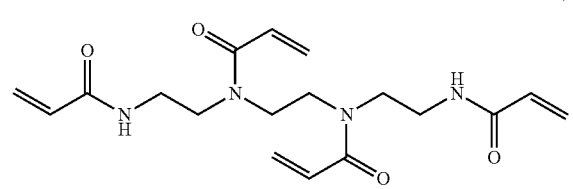

(5)

[Chemical Formula 8]

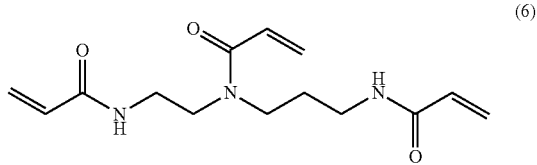

(6)

[Chemical Formula 9]

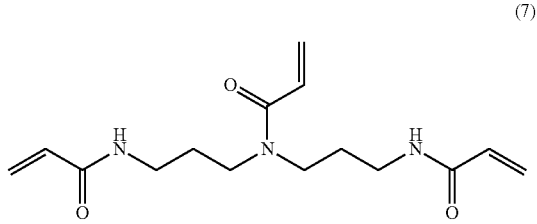

(7)

Among these, a tetra or more functional (meth)acrylamide-based polymerizable monomer is preferable, the polymerizable monomer represented by the above formula (1) is more preferable, and the polymerizable monomer represented by the above formula (2) is further preferable, and a polymerizable monomer represented by the above formula (2) in which all $R^1$s are hydrogen atoms in the formula is most preferable. In the two-paste type dental resin-reinforced glass ionomer cement composition of the present invention, it is preferable that tri or more functional (meth) acrylamide-based polymerizable monomer other than tetra or more functional (meth)acrylamide-based polymerizable monomer is not contained. In the two-paste type dental resin-reinforced glass ionomer cement composition of the present invention, it is preferable that tri or more functional (meth)acrylamide-based polymerizable monomer other than polymerizable monomer by the above formula (1) is not contained. In the two-paste type dental resin-reinforced glass ionomer cement composition of the present invention, it is preferable that tri or more functional (meth)acrylamide-based polymerizable monomer other than polymerizable monomer by the above formula (2) is not contained. In the two-paste type dental resin-reinforced glass ionomer cement composition of the present invention, it is preferable that tri or more functional (meth)acrylamide-based polymerizable monomer other than polymerizable monomer by the above formula (2) in which all $R^1$s are hydrogen atoms is not contained.

Any known photopolymerization initiators and/or chemical polymerization initiators can be used as the (f) polymerization initiator that can be used in the two-paste type dental resin-reinforced glass ionomer cement composition of the present invention, without any limitation.

Examples of the photopolymerization initiator includes photosensitizers and photosensitizer/photopolymerization promotor or the like. Specific examples of thephotosensitizer may include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenone as such as benzophenone, p-chlorobenzophenone and p-methoxybenzophenone; acylphosphineoxides such as 2,4,6-trimethylbenzoyl diphenylphosphineoxide, bis (2,4,6-trimethylbenzoyl) phenylphosphine oxide, 2,6-dimethoxybenzoyl diphenylphosphineoxide and bis(2,6-dimethoxybenzoyl)phenylphosphineoxide;
α-aminoacetophenones such as 2-benzyl-dimethylamino-1-(4-morpholinophenyl)-butanone-1,2-benzyl-diethyl-amino-1-(4-morpholinophenyl)propanone-1; ketals such as benzyldimethylketal, benzyldiethylketal and benzyl(2-methoxyethylketal); coumarins such as 3-(4-methoxybenzoyl)coumarin, 3-benzoyl-5,7-dimethoxycoumarin, 3,3'-carbonyl bis(7-diethylaminocoumarin) and 3,3'-carbonyl bis(7-dibutylaminocoumarin), and titanocenes such as bis (cyclopentadienyl)-bis[2,6-difluoro-3-(1-pyrolyl)phenyl] titanium, bis(cyclopentadienyl)-bis(pentanefluorophenyl) titanium and bis(cyclopentadienyl)-bis(2,3,5,6-tetrafluoro-4-disiloxyphenyl)-titanium, but are not limited to.

Specific examples of the photopolymerization promotors may include tetriary amine s such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethyl aminobenzoic acid, ethyl p-dimethylaminobenzoate, isoamyl p-dimethylaminobenzoate, N,N-dimethylanthranilic acid methyl ester, N,N-dihydroxyethylaniline, N,N-dihydroxyethyl-p-toluidine, p-dimethylaminophenyl alcohol, p-dimethylaminostyrene, N,N-dimethyl-3,5-xylidine, 4-dimethylaminopyridine, N,N-dimethyl-α-naphthylamine, N,N-dimethyl-β-naphthylamine, triethanolamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, 2,2'-(n-butyl imino)diethanol and other tertiary amines; secondary amines such as N-phenylglycine; barbiturates such as 5-butylbarbituric acid, 1-benzyl-5-phenylbarbituric acid, 1,3,5-trimethylbarbituric acid, sodium 1,3,5-trimethylbarbituric acid, calcium 1,3,5-trimethylbarbituric acid; tin compounds such as dibutyltin diacetate, dibutyltin dilaurate, dioctyltin dilaurate, dioctyltin diversate, dioctyltin bis(mercaptoacetic acid isooctyl ester) salt, and tetramethyl-1,3-diacetoxydistannoxane; aldehyde compounds such as lauryl aldehyde and terephthalaldehyde; and sulfur-containing compounds such as dodecyl mercaptan, 2-mercaptobenzoxazole, 1-decanethiol and thiosalicylic acid, but are not limited to.

In order to enhance photopolymerization promotion performances, it is effective to add, in addition to the above photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid and dimethylolpropionic acid, but are not limited to.

Examples of chemical polymerization initiators include redox type polymerization initiator systems comprising an peroxide/an amine compound, an peroxide/an amine compound/a aromatic sulfinic acid or a salt thereof or aromatic sulfonyl compounds, an peroxide/an amine compound/a (thio)barbituric acid compound or a (thio)barbituric acid compound, a peroxide/an amine compound/a borate compound, a peroxide/an ascorbic acid compound, a peroxide/a thiourea/a vanadium compounds or a copper compounds, an organometal type initiator systems that initiate polymerization by reacting with oxygen or water. Further examples include aromatic sulfinates, borate compounds, and (thio) barbiturates which can initiate polymerization by reacting with an acidic compound, but are not limited thereto.

Examples of the peroxide include sodium peroxodisulfate, potassium peroxodisulfate, ammonium peroxodisulfate, sodium peroxodiphosphate, potassium peroxodiphosphate, ammonium peroxodiphosphate, benzoyl peroxide, p-chlorobenzoyl peroxide, 2,4-dichlorobenzoyl peroxide, diacetyl peroxide, lauroyl peroxide, di-t-butyl peroxide, dicumyl peroxide, cumene hydroperoxide, t-butyl hydroperoxide, 1,1,3,3-tetra methyl butyl hydroperoxide, t-amyl hydroperoxide, iso-propylbenzene hydroperoxide, 5-phenyl-4-pentenyl hydroperoxide, t-butylperoxyisopropyl carbonate, methyl ethyl ketone peroxide, 1,1-bis(t-butylperoxy) cyclohexane, 1,1-bis(t-hexylperoxy)cyclohexane and t-butylperoxybenzoate, but are not limited to.

The amine compound is preferably an aromatic secondary or aromatic tertiary amine, and specific examples thereof include N-methyl-p-toluidine, N-(2-hydroxyethyl)-p-toluidine, ethyl p-methylaminobenzoate, N-methylaniline, N-(2-hydroxyethyl)aniline, N,N-dimethyl-p-toluidine, N,N-diethyl-p-toluidine, N,N-bis(2-hydroxyethyl)-p-toluidine, ethyl p-dimethylaminobenzoate, N,N-dimethylaniline, N,N-bis (2-hydroxyethyl)aniline, but are not limited to.

Examples of an aromatic sulfinic acid or a salt thereof or the aromatic sulfonyl compound include benzene sulfinic acid, p-toluene sulfinic acid, o-toluene sulfinic acid, 2,4,6-trimethylbenzene sulfinic acid, 2,4,6-triisopropylbenzene sulfinic acid, and its sodium salt, potassium salt, lithium salt or ammonium salt, benzenesulfonyl chloride, benzene sulfonyl fluoride, benzenesulfonamide, benzene sulfonyl hydrazide, p-toluene sulfonyl chloride, p-toluene sulfonyl fluoride, p-toluene sulfonamide, p-toluenesulfonyl hydrazide and the like, but are not limited to.

Examples of a (thio)barbituric acid compound or the (thio)barbituric acid salt compound include barbituric acid, 1,3-dimethylbarbituric acid, 1,3-diphenylbarbituric acid, 1,5-dimethylbarbituric acid, 5-butyl barbituric acid, 5-ethyl barbituric acid, 5-isopropyl barbituric acid, 5-cyclohexyl barbituric acid, 5-lauryl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl-5-cyclohexyl barbituric acid, 1,3-dimethyl-5-phenyl barbituric acid, 1-cyclohexyl-5-ethyl barbituric acid, 1-phenyl-5-benzyl barbituric acid, 1-benzyl-5-phenyl barbituric acid, thiobarbituric acid, 1,3-dimethyl-thiobarbituric acid, 5-phenylthiobarbituric acid and its alkali metal salts (lithium, sodium, potassium salts and the like), alkaline earth metal salts (calcium, strontium, barium salts and the like), ammonium salts, tetramethylammonium salts, and tetraethylammonium, but are not limited there to.

Examples of the borate compound include trialkylphenylboron, trialkyl(p-chlorophenyl)boron, trialkyl(p-fluorophenyl)boron, trialkyl(p-butylphenyl)boron, trialkyl(p-butyloxyphenyl)boron, monoalkyltriphenylboron, monoalkyltris (p-chlorophenyl)boron, monoalkyltris(p-fluorophenyl)boron, monoalkyltris(p-butylphenyl)boron, monoalkyltris(p-butyloxyphenyl)boron, tetraphenylboron, tetrakis(p-chlorophenyl)boron, tetrakis(p-fluorophenyl)boron, tetrakis(p-butylphenyl)boron, tetrakis(p-butyloxyphenyl)boron (wherein the alkyl group is n-butyl group, n-octyl group, n-dodecyl group and the like) and sodium salt, potassium salt, lithium salt, magnesium salt, tetramethylammonium salt, tetraethylammonium salt, tetrabutylammonium salt, methylpyridinium salt, ethylpyridinium salt, methylquinolinium, ethylquinolinium salt thereof and the like but are not limited to.

Examples of ascorbic acid compounds include L(+)-ascorbic acid, isoascorbic acid, L(+)-sodium ascorbate, L(+)-potassium ascorbate, L(+)-calcium ascorbate, sodium isoascorbate and the like, but are not limited to.

Examples of thiourea compounds include 1, 3-dimethyl-thiourea, tetramethylthiourea, 1,1-diethylthiourea, 1,1,3,3-tetraethylthiourea, 1-allyl-2-thiourea, 1,3-diallylthiourea, 1,3-dibutylthiourea, 1,3-diphenyl-2-thiourea, 1,3-dicyclohexylthiourea, ethylenethiourea, N-methylthiourea, N-phenylthiourea, N-benzoylthiourea, N-acetylthiourea and the like, but are not limited to.

Examples of vanadium compounds include vanadium acetylacetonate, vanadyl acetylacetonate, vanadyl stearate, vanadium naphthenate, vanadium benzoylacetonate and the like, but are not limited to.

Examples of the copper compound include copper chloride, copper acetate, copper naphthenate, copper salicylate, copper gluconate, copper oleate, copper benzoate, copper acetylacetonate, and copper naphthenate and the like, but are not limited to.

Example of the organometal type polymerizable initiators may include organic boron compounds such as triphenylborane, tributylborane, and a partial oxide of tributylborane and the like, but are not limited to.

These polymerization initiators can be used not only singly but also in combinations of two or more, regardless of the polymerization manner or the polymerization method. In addition, there is no problem even if these polymerization initiators are subjected to a secondary treatment such as encapsulation in a microcapsule, if necessary.

The two-paste type dental resin-reinforced glass ionomer cement composition of the present invention can contain (g) acidic group-containing polymerizable monomer, if desired, in order to improve the adhesive property to the tooth substance, base metal, alumina, zirconia and the like. The acidic group-containing polymerizable monomer can be the same as the acidic group-containing polymerizable monomer that can be used to obtain the (b) polymer of acidic group-containing polymerizable monomer. In the present invention, it is preferable that the (g) acidic group-containing polymerizable monomer is different from the acidic group-containing polymerizable monomer which may be used for obtaining the (b) polymer of an acid group-containing polymerizable monomer. The acidic group-containing polymerizable monomer may be used not only singly but also in combinations of a plurality thereof without any problem.

Among them, the acidic group-containing polymerizable monomer is preferably a carboxyl group-containing polymerizable monomer, and more preferably has two or more carboxyl groups. By containing a carboxyl group-containing polymerizable monomer, it becomes easy to obtain a two-paste type dental resin-reinforced glass ionomer cement composition having an excellent balance of adhesive property to tooth substance and mechanical properties.

The main components of the two-paste type dental resin-reinforced glass ionomer cement composition of the present invention is described above the (a) acid-reactive glass powder, the (b) polymer of acidic group-containing polymerizable monomer, the (c) water, the (d) hydroxyl group-containing (meth)acrylate-based polymerizable monomer, the (e) tri or more functional (meth)acrylamide-based polymerizable monomer, the (f) polymerization initiator, and (g) acidic group-containing polymerizable monomer, and preferable contents are follows.

The content of the (a) acid-reactive glass powder is preferably 10 to 55 parts by weight in 100 parts by weight of the total weight of the composition, more preferably 25 to 40 parts by weight. When the content of the acid-reactive glass powder is less than 10 part by weight, there is a case the mechanical strength of the set product may tend to decrease too much to cause problems in durability of the set product. When the content of acid-reactive glass powder exceeds 55 part by weight, there is a case that viscosity of the mixed material may become higher to cause problem in operability. Further, there is a case that because the setting rate became faster, a sufficient operation surplus time is not obtained.

The content of the (b) polymer of acidic group-containing polymerizable monomer is preferably 0.1 to 30 parts by weight in 100 parts by weight of the total weight of the composition, more preferably 1.0 to 20 parts by weight. When the content of the polymer of acidic group-containing polymerizable monomer is less than 0.1 part by weight, there is a case that the acid-base reaction is less likely to occur to cause curing failure. When the content of the polymer of acidic group-containing polymerizable monomer exceeds 30 part by weight, there is a case that viscosity of the mixed material may become higher to cause problem in operability. Further, there is a case that because the setting rate become faster, a sufficient operation surplus time is not obtained.

The content of the (c) water is preferably 1 to 30 parts by weight in 100 parts by weight of the total weight of the composition, more preferably 5 to 25 parts by weight. When the content of the water is less than 1 part by weight, there is a case that the acid-base reaction is less likely to occur to cause setting failure. When the content of the water exceeds 30 part by weight, there is a case the mechanical strength of the set product may be too low to cause a problem in durability.

The content of the (d) hydroxyl group-containing (meth)acrylate-based polymerizable monomer is preferably 3 to 60 parts by weight in 100 parts by weight of the total weight of the composition, more preferably 15 to 50 parts by weight. When the content of the hydroxyl group-containing (meth)acrylate-based polymerizable monomer is less than 3 part by weight, there is a case that the compatibility of each polymerizable monomer, water and the polymer of acidic group-containing polymerizable monomer becomes poor and the set product becomes non-uniform, and therefore the mechanical properties and transparency may deteriorate. When the content of the hydroxyl group-containing (meth)acrylate-based polymerizable monomer exceeds 60 part by weight, there is a case that the curability of the polymerizable monomer mixture may deteriorate and the mechanical properties may deteriorate.

The content of the (e) tri or more functional (meth)acrylamide-based polymerizable monomer is preferably 0.5 to 30 parts by weight in 100 parts by weight of the total weight of the composition, more preferably 2.0 to 12.5 parts by weight, most preferably 5 to 12.5 parts by weight. When the content of the tri or more functional (meth)acrylamide-based polymerizable monomer is less than 0.5 part by weight, there is a case that the curability of the polymerizable monomer mixture may deteriorate and the mechanical properties may deteriorate. Further, there is a case that preservation stability may deteriorate. When the content of the tri or more functional (meth)acrylamide-based polymerizable monomer exceeds 30 part by weight, there is a case that the compatibility of each polymerizable monomer, water and the polymer of acidic group-containing polymerizable monomer becomes poor and the set product becomes non-uniform, and therefore the mechanical properties and transparency may deteriorate.

The content of the (f) polymerization initiator is preferably 0.1 to 10 parts by weight in 100 parts by weight of the total weight of the composition, more preferably 0.4 to 2.0 parts by weight. When the content of the polymerization initiator is less than 0.1 part by weight, there is a case that the curability may deteriorate and the mechanical properties may deteriorate. When the content of the polymerization initiator exceeds 10 part by weight, there is a case that preservation stability may deteriorate.

The content of the (g) acidic group-containing polymerizable monomer is preferably 0.1 to 10 parts by weight in 100 parts by weight of the total weight of the composition, more preferably 0.5 to 6 parts by weight. When the content of the acidic group-containing polymerizable monomer is less than 0.1 parts by weight, there is a case that adhesive property to tooth substances deteriorates. When the content of the acidic group-containing polymerizable monomer exceeds 10 part by weight, there is a case that the curability may deteriorate and the mechanical properties may deteriorate. Further, there is a case that preservation stability may deteriorate.

Furthermore, the two-paste type dental resin-reinforced glass ionomer cement composition of the present invention may contain a thickener to such a range that various properties are not adversely affected, for the purpose of adjusting pasty property. As the thickener which can be used in the two-paste type dental resin-reinforced glass ionomer cement composition of the present invention, any of an inorganic thickener and an organic thickener can be used.

Specific examples of an inorganic thickener include fumed silica, calcium carbonate, calcium silicate, magnesium silicate, and a clay mineral such as saponite, montmorillonite, beidellite, vermiculite, sauconite, stevensite, hectorite, smectite, nekutaito and sepiolite, but are not limited to.

Specific examples of an organic thickener include methyl cellulose, hydroxyethyl cellulose, hydroxymethyl cellulose, hydroxypropyl cellulose, carboxymethyl cellulose, sodium carboxymethyl cellulose, calcium carboxymethyl cellulose, carboxypolymethylene, sodium alginate, propylene glycol alginate ester, sodium polyacrylate, starch, starch sodium glycolate, starch phosphate ester, polyvinyl pyrrolidone, carboxyvinyl polymer, khaya gum, arabic gum, karaya gum, guar gum, but are not limited to. These thickeners may be used alone or as a mixture of two or more thereof.

It is preferable that the content of the thickener in each paste is within a range of 0.1 to 20.0 wt. %.

The two-paste type dental resin-reinforced glass ionomer cement composition of the present invention may contain other polymerizable monomer other than the (d) hydroxyl group-containing (meth)acrylate-based polymerizable monomer, the (e) tri or more functional (meth)acrylamide-based polymerizable monomer and the (g) acidic group-containing polymerizable monomer to such a range that various properties are not adversely affected, for the purpose of improving mechanical properties. As such polymerizable monomer, known polymerizable monomers may be used regardless of the number or the type of radical polymerizable unsaturated groups (monofunctional groups or multifunctional). Specific examples of the polymerizable monomer having a (meth) acryloyl group as an unsaturated group are listed below as representative example.

Examples of the monofunctional polymerizable monomer include methyl(meth)acrylate, ethyl(meth)acrylate, butyl(meth)acrylate, hexyl(meth)acrylate, glycidyl(meth)acrylate, lauryl(meth)acrylate, cyclohexyl(meth)acrylate, allyl(meth)acrylate, 2-ethoxyethyl(meth)acrylate, methoxypolyethyleneglycol(meth)acrylate, isopropyl(meth)acrylate, isobutyl(meth)acrylate, 2-ethylhexyl(meth)acrylate, tetrahydrofurfuryl(meth)acrylate, benzyl(meth)acrylate, isobornyl(meth)acrylate and the like, but are not limited to.

Examples of the aromatic bifunctional polymerizable monomer include 2,2-bis(4-(meth)acryloyloxyphenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2 (4-(meth)acryloyloxydiethoxyphenyl)prop ane, 2(4-(meth)acryloyloxydiethoxyphenyl)-2(4-(meth)acryloyloxytriethoxyphenyl)propane, 2 (4-(meth)

acryloyloxydipropoxyphenyl)-2 (4-(meth)acryloyloxytriethoxyphenyl)prop ane, 2,2-bis(4-(meth)acryloyloxydipropoxyphenyl)propane, 2,2-bis(4-(meth)acryloyloxyisopropoxyphenyl)propane, 2,2-bis(4-(meth)acryloyloxypolyethoxyphenyl)propane, 9,9-bis[4-(2-acryloyloxyethoxy)phenyl]fluorine and the like, but are not limited to.

Examples of the aliphatic bifunctional polymerizable monomer include ethyleneglycoldi(meth)acrylate, diethyleneglycoldi(meth)acrylate, triethyleneglycoldi(meth)acrylate, tetraethyleneglycoldi(meth)acrylate, polyethyleneglycoldi(meth)acrylate, neopentylglycoldi(meth)acrylate, propyleneglycoldi(meth)acrylate, dipropyleneglycoldi(meth)acrylate, tripropylene glycol di(meth)acrylate, tricyclodecane dimethanol di(meth)acrylate, 1,3-butanediol di(meth)acrylate, 1,4-butanediol di(meth)acrylate, 1,6-hexanediol di(meth)acrylate, 1,9-nonanediol di(meth)acrylate, 1,10-decanediol di(meth)acrylate and the like, but are not limited to.

Examples of the tri functional polymerizable monomer include trimethylolpropane tri(meth)acrylate, trimethylolethane tri(meth)acrylate, and trimethylolmethan tri(meth)acrylate, but are not limited to.

Examples of a tetra functional polymerizable monomer include pentaerythritol tetra(meth)acrylate and ditrimethylolporpane tetra (meth)acrylate, but are not limited to.

Examples of a urethane type polymerizable monomer include di(meth)acrylates having a bifunctional or tri or higher functional urethane bond, derived from an adduct of a hydroxyl group-containing polymerizable monomer such as 2-hydroxyethyl (meth)acrylate, 2-hydroxypropyl (meth)acrylate and 3-chloro-2-hydroxypropyl (meth)acrylate and a diisocyanate compound such as methylcyclohexane diisocyanate, methylenebis(4-cyclohexylisocyanate), hexamethylene diisocyanate, trimethylhexamethylene diisocyanate, isophorone diisocyanate, diisocyanate methylbenzene and 4,4-diphenylmethane diisocyanate, but are not limited to.

In addition to the above described (meth)acrylate group-containing polymerizable monomer, a polymerizable monomer having a sulfur atom in the molecule, a polymerizable monomer having a fluoro group, and an oligomer or polymer having at least one polymerizable group can be used. These polymerizable monomers may be used alone or in combination of two or more as necessary.

Further, a polymerizable monomer having one or two (meth)acrylamide groups in the molecule can be contained in the two-paste type dental resin-reinforced glass ionomer cement composition of the present invention to such a range that various properties are not adversely effected, without any problem.

It is preferable that the content of the other polymerizable monomer other than the (d) hydroxyl group-containing (meth)acrylate-based polymerizable monomer, the (e) tri or more functional (meth)acrylamide-based polymerizable monomer and the (g) acidic group-containing polymerizable monomer is within a range of 10.0 part by weight or less in 100 parts by weight of the total weight of the composition.

For the purpose of controlling the acid-base reaction of the (a) acid-reactive glass powder and the (b) polymer of acidic group-containing polymerizable monomer, and adjusting the operation surplus time and setting time, the two-paste type dental resin-reinforced glass ionomer cement composition of the present invention may contain a polybasic carboxylic acid, a phosphoric acid, a pyrophosphoric acid or a tripolyphosphoric acid, but not limited to.

Specific examples of the polybasic carboxylic acid used in the two-paste type dental resin-reinforced glass ionomer cement composition of the present invention include tartaric acid, citric acid, maleic acid, fumaric acid, malic acid, aconitic acid, tricarballylic acid, itaconic acid, 1-butene-1,2,4-tricarboxylic acid, and 3-butene-1,2,3-tricarboxylic acid, and the like. The aforementioned polybasic carboxylic acid are not limited to these, but can be used without any limitation.

A polybasic carboxylic acid, a phosphoric acid, a pyrophosphoric acid and/or a tripolyphosphoric acid may be used alone or in combination of two or more thereof. A content of the polybasic carboxylic acid, the phosphoric acid, the pyrophosphoric acid and/or the tripolyphosphoric acid is preferably in the range from 0.1 to 15.0 part by weight in 100 parts by weight of the total weight of the composition.

Further, a surfactant can be contained in the two-paste type dental resin-reinforced glass ionomer cement composition of the present invention to such a range that various properties are not adversely affected, for the purpose of improving mixability. The surfactant which can be used in the two-paste type dental resin-reinforced glass ionomer cement composition of the present invention may be any of an ionic surfactant and a nonionic surfactant.

Specific examples of the anionic surfactant in the ionic surfactant include aliphatic carboxylic acid metal salts such as sodium stearate, sulfated aliphatic carboxylic acid metal salts such as sodium dioctyl sulfosuccinate, and metal salts of higher alcohol sulfate ester such as sodium stearyl sulfate.

In addition, examples of the cationic surfactant include an adduct of higher alkylamine and ethylene oxide, amines made from lower amine, and alkyltrimethylammonium salts such as lauryltrimethylammoniun chloride. Further, examples of the amphoteric surfactant include metal salts of higher alkylaminopropionic acid such as sodium stearylaminopropionate, and betaines such as lauryldimethylbetaine.

Examples of the nonionic surfactant include polyethylene glycol type and polypropylene glycol type in which ethylene oxide or propylene oxide is added to higher alcohols, alkyl phenols, fatty acids, higher fatty amines, or aliphatic amides, and polyhydric alcohol type in which a fatty acid are ester bonded to polyhydric alcohols, diethanolamines, or saccharides.

The aforementioned surfactants are not limited to these, but can be used without any limitation. These surfactants can be used alone or in a combination of a few kinds. It is preferable the content of the surfactant is 0.001 to 5.0 parts by weight in 100 parts by weight of the total weight of the composition.

Further, a non-acid reactive powder can be contained in the two-paste type dental resin-reinforced glass ionomer cement composition of the present invention to such a range that various properties are not adversely affected, for the purpose of adjusting operability, a mechanical characteristic or a curing characteristic.

As the non-acid reactive powder used in the two-paste type dental resin-reinforced glass ionomer cement composition of the present invention, any non-acid reactive powder as long as the non-acid reactive powder does not contain element which may react with an acid group of the acid group-containing polymerizable monomer can be used without any limitation.

Examples of the non-acid reactive powder include known dental fillers such as an inorganic filler, an organic filler and an organic-inorganic composite filler, and these can be used alone or in a combination of a few of them without any limitation. Among them, it is especially preferable that an inorganic filler is used. In addition, a shape of these non-acid reactive powder is not particularly limited, but arbitral particle shapes such as spherical, needle-like, plate-like, ground-like, and scaly-shapes and aggregate thereof may be used. An average particle diameter of the non-acid reactive powder is not particular limited, but is preferably within a range of 0.001 to 30 μm.

Specific examples of the inorganic filler include quartz, amorphous silica, ultrafine silica, various glasses which does not contain element which may react with an acid group (including a glass by melting method, synthetic glass by sol-gel method, a glass produced by a vapor phase reaction, and the like), silicon nitride, silicon carbide, boron carbide and the like, but is not limited thereto.

It is preferable that the content of the non-acid reactive powder is 0.001 to 40 parts by weight in 100 parts by weight of the total weight of the composition.

In the two-paste type dental resin-reinforced glass ionomer cement composition of the present invention, known various additives can be arbitrarily mixed if necessary. Examples of such additives which can be used in the present invention include a polymerization inhibitor, a chain transfer agent, a colorant, a discoloration preventing agent, a fluorescent agent, an ultraviolet absorber, an antibacterial agent and an antiseptic agent.

It is preferable that two-paste type dental resin-reinforced glass ionomer cement composition of the present invention consists of the (a) acid-reactive glass powder, the (b) polymer of acidic group-containing polymerizable monomer, the (c) water, the (d) hydroxyl group-containing (meth)acrylate-based polymerizable monomer, the (e) tri or more functional (meth)acrylamide-based polymerizable monomer, and the (f) polymerization initiator.

It is preferable that two-paste type dental resin-reinforced glass ionomer cement composition of the present invention consists of the (a) acid-reactive glass powder, the (b) polymer of acidic group-containing polymerizable monomer, the (c) water, the (d) hydroxyl group-containing (meth)acrylate-based polymerizable monomer, the (e) tri or more functional (meth)acrylamide-based polymerizable monomer, the (f) polymerization initiator, and the (g) acidic group-containing polymerizable monomer.

It is preferable that two-paste type dental resin-reinforced glass ionomer cement composition of the present invention consists of the (a) acid-reactive glass powder, the (b) polymer of acidic group-containing polymerizable monomer, the (c) water, the (d) hydroxyl group-containing (meth)acrylate-based polymerizable monomer, the (e) tri or more functional (meth)acrylamide-based polymerizable monomer, the (f) polymerization initiator, the (g) acidic group-containing polymerizable monomer, and at least one arbitrary component selected from the group consisting of a polybasic carboxylic acid, a phosphoric acid, a pyrophosphoric acid or a tripolyphosphoric acid, a surfactant, a non-acid reactive powder, a polymerization inhibitor, a chain transfer agent, a colorant, a discoloration preventing agent, a fluorescent agent, an ultraviolet absorber, an antibacterial agent and an antiseptic agent.

EXAMPLES

Hereinafter, the present invention will be described in detail with reference to Examples and Comparative Examples. However, the present invention is not limited to these Examples. The components (a) to (g) and other components used for preparing the two-paste type dental resin-reinforced glass ionomer cement compositions of Examples and Comparative Examples, and their abbreviations are as follows.

[(a) acid-reactive glass powder]
CK-Si-1: Silane-treated fluoroaluminosilicate glass powder 1
(50% particle diameter: 3.3 μm)
CK-Si-2: Silane-treated fluoroaluminosilicate glass powder 2
(50% particle diameter: 1.0 μm)
[(b) polymer of acidic group-containing polymerizable monomer]
PCA1: acrylic acid-3-butene-1,2,3-tricarboxylic acid copolymer powder (weight average molecular weight: 80,000)
PCA2: acrylic acid homopolymer powder (weight average molecular weight: 50,000)
[(c) water]
Distilled water
[(d) hydroxyl group-containing (meth)acrylate-based polymerizable monomer]
HEMA: 2-hydroxyethyl methacrylate
Bis-GMA: bisphenol A diglycidyl methacrylate
CDMA: glycerin dimethacrylate
GDA: 2-hydroxy-3-acryloyloxypropyl methacrylate
[(e) tri or more functional (meth)acrylamide-based polymerizable monomer]
<Tetra functional acrylamide polymerizable monomer>
FAM-401 (manufactured by FUJIFILM Corporation): a compound represented by formula (2) in which all $R^1$s are hydrogen atoms
FAM-402 (manufactured by FUJIFILM Corporation): compound represented by formula (5)
<Tri functional acrylamide polymerizable monomer>
FAM-301 (manufactured by FUJIFILM Corporation): compound represented by formula (4)
FAM-302L (manufactured by FUJIFILM Corporation): compound represented by formula (7)
[(f) polymerization initiator]
CQ: dl-camphorquinone
BPO: benzoyl peroxide
DMBE: ethyl p-dimethylaminobenzoate
DEPT: N,N-bis(2-hydroxyethyl)-p-toluidine
CHP: cumene hydroperoxide
TPB-Na: tetraphenylboron sodium salt
KPS: potassium peroxodisulfate
AA: ascorbic acid
[(g) acidic group-containing polymerizable monomer]
4-MET: 4-methacryloxyethyl trimellitic acid
4-META: 4-methacryloxyethyl trimellitic anhydride
4-AET: 4-acryloxyethyl trimellitic acid
10-MDP: 10-methacryloyloxydecyl dihydrogen phosphate
[Others]
UDMA: urethane dimethacrylate
HEAR: hydroxyethyl acrylamide
2AM: N,N'-methylene bismethacrylamide
AEROXIDE AluC: aluminum oxide having average particle diameter of about 13 nm
Aerosil R972: fumed silica having average particle diameter of about 16 nm
Aerosil #200: fumed silica having average particle diameter of about 12 nm
BHT: dibutylhydroxytoluene The preparing method of the fluoroaluminosilicate glass powder is as follows.
[Preparation of Fluoroaluminosilicate Glass Powder 1]
Various raw materials: silicon dioxide, aluminum oxide, sodium fluoride, and strontium carbonate (glass composition: $SiO_2$: 26.4 wt. %, $Al_2O_3$: 29.3 wt. %, SrO: 20.5 wt. %, $P_2O_5$: 10.9 wt. %, $Na_2O$: 2.5 wt. %, and F: 10.4 wt. %) were mixed and the mixed material was molten at 1400° C. in a melting furnace. The melt was taken out from the melting furnace and was quenched in water to prepare a glass. The resulting glass was pulverized to obtain fluoroaluminosilicate glass powder 1. The glass powder was measured for an average particle diameter by a laser diffraction type grain size measuring apparatus (Microtrac MT3300EXII: NIKKISO Co., Ltd.). The result was 3.3 µm.

[Preparation of Fluoroaluminosilicate Glass Powder 2]

A glass was prepared by the same method as fluoroaluminosilicate glass powder 1, and the pulverizing time was adjusted to obtain a fluoroaluminosilicate glass powder 2 having a 50% particle diameter of 1.0 µm.

The silane treatment method of fluoroaluminosilicate glass powders is as follows.

[Silane Treatment of Fluoroaluminosilicate Glass Powders 1 and 2]

The fluoroaluminosilicate glass powder 1 or 2 of 200 g was dispersed in 500 mL of water, 2 g of 3-methacryloyloxypropyltrimethoxysilane was added, and the mixture was stirred at room temperature for 2 hours. After the solvent was distilled off under reduced pressure, it was further dried at 100° C. for 5 hours to obtain silane-treated fluoroaluminosilicate glass powders 1 and 2: CK-Si-1 and CK-Si-2.

[Preparation of Paste Material]

The components were mixed in the ratios shown in Tables 1 to 2 to prepare each paste (first paste and second paste) of the two-paste type dental resin-reinforced glass ionomer cement composition used in Examples and Comparative Examples.

TABLE 1

First paste of paste materials used in Examples and Comparative Examples (parts by weight)

| | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| (a) acid-reactive glass powder | CK-Si-1 | 60 | 65 | 50 | | 25 | | | | | | |
| | CK-Si-2 | | 10 | 20 | 50 | 50 | 50 | 50 | 50 | 50 | 50 | 50 |
| (b) polymer of acidic group-containing polymerizable monomer | PCA1 | | | | | | | | | | | |
| | PCA2 | | | | | | | | | | | |
| (c) water | Distilled water | | | | | | | | | | 11 | |
| (d) hydroxyl group-containing (meth)acrylate-based polymerizable monomer | HEMA | 17.5 | 14 | 10 | 8.2 | 11 | 25.7 | 28 | 27.7 | 25.7 | 17 | 24.7 |
| | GDMA | 17.4 | | 13.7 | 25 | 9.8 | 10 | 10 | 10 | 10 | 10 | 10 |
| | GDA | | 5 | | | | | | | | | |
| | Bis-GMA | | 2.19 | | | | | | | | | |
| (e) tri or more functional (meth)acrylamide-based polymerizable monomer | FAM-301 | | | | | | | | | | | |
| | FAM-302L | | | | | | | | | | | |
| | FAM-401 | | | | | | 5 | 5 | 5 | 5 | 5 | 5 |
| | FAM-402 | | | | | | | | | | | |
| (f) polymerization initiator | CQ | | 0.3 | 0.3 | 0.3 | 0.3 | 0.3 | | 0.3 | 0.3 | | 0.3 |
| | TPB-Na | 0.1 | | | | 0.9 | 1 | 2 | 2 | 1 | 2 | 1 |
| | DEPT | 0.5 | | 0.5 | | | | | | | | |
| | DMBE | | 0.5 | 0.5 | 0.5 | | | | | | | |
| | AA | | 0.01 | | | | | | | | | |
| (g) acidic group-containing polymerizable monomer | 4-MET | | | | | | | | | | | |
| | 10-MDP | | | | | | | | | | | |
| | 4-META | | | | | | | | | | | |
| | 4-AET | | | | | | | | | | | |
| Others | AEROXIDE AluC | 4.5 | 3 | 5 | 6 | 3 | 8 | 5 | 5 | 8 | 5 | 8 |
| | UDMA | | | | 10 | | | | | | | |

| | | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| (a) acid-reactive glass powder | CK-Si-1 | | | | | 15 | 50 | | | 25 | | 65 |
| | CK-Si-2 | 20 | 10 | 77.7 | 50 | 50 | 20 | 25 | 15 | 50 | 50 | 10 |
| (b) polymer of acidic group-containing polymerizable monomer | PCA1 | | | | | | | | | | | |
| | PCA2 | | | | | | | | | | | |
| (c) water | Distilled water | | | | 5 | | | | | | | |
| (d) hydroxyl group-containing (meth)acrylate-based polymerizable monomer | HEMA | 27.7 | 27.7 | 14 | 25.7 | 11 | | 53 | 63 | 11 | 25.7 | 14 |
| | GDMA | 10 | 10 | | 10 | 9.8 | 3 | 10 | 10 | 9.8 | 10 | |
| | GDA | | | | | | | | | | | 5 |
| | Bis-GMA | | | | | | | | | | | 2.19 |
| (e) tri or more functional (meth)acrylamide-based polymerizable monomer | FAM-301 | | | | | | | | | | | |
| | FAM-302L | | | | | | | | | | | |
| | FAM-401 | 5 | 5 | | 5 | | | 5 | 5 | | 5 | |
| | FAM-402 | | | | | | | | | | | |
| (f) polymerization initiator | CQ | 0.3 | 0.3 | 0.3 | 0.3 | 0.3 | 0.3 | | | 0.3 | 0.3 | 0.3 |
| | TPB-Na | 2 | 2 | 2 | 1 | 0.9 | 3 | 2 | 2 | 0.9 | 1 | |
| | DEPT | | | | | | | | | | | |
| | DMBE | | | | | | | | | | | 0.5 |
| | AA | | | | | | | | | | | 0.01 |

TABLE 1-continued

First paste of paste materials used in Examples and Comparative Examples (parts by weight)

|     |                                            |                                       |     |     |     |     |     |      |     |     |     |     |
| --- | ------------------------------------------ | ------------------------------------- | --- | --- | --- | --- | --- | ---- | --- | --- | --- | --- |
| (g) | acidic group-containing polymerizable monomer | 4-MET<br>10-MDP<br>4-META<br>4-AET |     |     |     |     |     |      |     |     |     |     |
|     | Others                                     | AEROXIDE AluC                         | 5   | 5   | 1   | 8   | 3   |      | 5   | 5   | 3   | 8   | 3 |
|     |                                            | UDMA                                  |     |     |     |     |     | 23.7 |     |     |     |     |

| | | Example 23 | Example 24 | Example 25 | Example 26 | Example 27 | Comparative Example 1 | Comparative Example 2 | Comparative Example 3 | Comparative Example 4 | Comparative Example 5 |
| --- | --- | --- | --- | --- | --- | --- | --- | --- | --- | --- | --- |
| (a) acid-reactive glass powder | CK-Si-1 | 65 | 65 | 65 | 65 | 60 | 60 | 65 | | | 65 |
| | CK-Si-2 | 10 | 10 | 10 | 10 | 10 | | 10 | 50 | 50 | |
| (b) polymer of acidic group-containing polymerizable monomer | PCA1 | | | | | | 5 | | | | |
| | PCA2 | | | | | | | | | | |
| (c) water | Distilled water | | | | 2.19 | | | | | | |
| (d) hydroxyl group-containing (meth)acrylate-based polymerizable monomer | HEMA | 14 | 18 | 18 | 14 | 14 | 17.5 | 14 | 20 | 21.3 | 24 |
| | GDMA | | | | | | 14.4 | | 20.7 | 20 | |
| | GDA | 5 | 1 | 1 | 5 | 5 | | 5 | | | 5 |
| | Bis-GMA | 2.19 | 2.19 | 2.19 | | 2.19 | | 2.19 | | | 2.19 |
| (e) tri or more functional (meth)acrylamide-based polymerizable monomer | FAM-301 | | | | | | | | | | |
| | FAM-302L | | | | | | | | | | |
| | FAM-401 | | | | | | | | | | |
| | FAM-402 | | | | | | | | | | |
| (f) polymerization initiator | CQ | 0.3 | 0.3 | 0.3 | 0.3 | 0.3 | | 0.3 | 0.3 | 0.3 | 0.3 |
| | TPB-Na | | | | | | 0.1 | | 2 | 0.9 | |
| | DEPT | | | | | | 0.5 | | | | |
| | DMBE | 0.5 | 0.5 | 0.5 | 0.5 | 0.5 | | 0.5 | | 0.5 | 0.5 |
| | AA | 0.01 | 0.01 | 0.01 | 0.01 | 0.01 | | 0.01 | | | 0.01 |
| (g) acidic group-containing polymerizable monomer | 4-MET | | | | | | | | | | |
| | 10-MDP | | | | | | | | | | |
| | 4-META | | | | | | | | | | |
| | 4-AET | | | | | | | | | | |
| Others | AEROXIDE AluC | 3 | 3 | 3 | 3 | 3 | 4.5 | 3 | 7 | 7 | 3 |
| | UDMA | | | | | | | | | | |

TABLE 2

Second paste of paste materials used in Examples and Comparative Examples (parts by weight)

| | | Example 1 | Example 2 | Example 3 | Example 4 | Example 5 | Example 6 | Example 7 | Example 8 | Example 9 | Example 10 | Example 11 |
| --- | --- | --- | --- | --- | --- | --- | --- | --- | --- | --- | --- | --- |
| (a) acid-reactive glass powder | CK-Si-1 | | | | | | | | | | | |
| | CK-Si-2 | | | | | | | | | | | |
| (b) polymer of acidic group-containing polymerizable monomer | PCA1 | 20 | 20 | 29.6 | 36 | | | | | | | |
| | PCA2 | | | | | 22.9 | 3.8 | 6.9 | 15 | 3.8 | 6.9 | 3.8 |
| (c) water | Distilled water | 20 | 20 | 30 | 38.4 | 50 | 15 | 11 | 26 | 10 | | 15 |
| (d) hydroxyl group-containing (meth)acrylate-based polymerizable monomer | HEMA | 35 | 25 | 20 | 10 | 12 | 35 | 37 | 22.6 | 41 | 48 | 36 |
| | GDMA | 5 | 5 | | | 4 | 20 | 20 | 10 | 20 | 20 | 20 |
| | Bis-GMA | 2 | 2.6 | | | | | | 1 | | | |
| (e) tri or more functional (meth)acrylamide-based polymerizable monomer | FAM-301 | 4.6 | | 7 | | | | | | | | |
| | FAM-302L | | | | 5 | | 20 | | | 20 | | 20 |
| | FAM-401 | | 10 | | 2 | | | 5 | 10 | | 5 | |
| | FAM-402 | | | | | | | 5 | | | 5 | |
| (f) polymerization initiator | BPO | 0.3 | 0.3 | 0.1 | | | 0.1 | | 0.3 | 0.1 | | 0.1 |
| | CHP | | | | 0.5 | 1 | | | | | | |
| | KPS | | | 0.2 | | | | | | | | |
| (g) acidic group-containing polymerizable monomer | 4-MET | 10 | 12 | | | | 1 | 10 | | 10 | | |
| | 10-MDP | | | 10 | | | | | 10 | | | |
| | 4-META | | | | 5 | | | | | | | |
| | 4-AET | | | | | 3 | | | | | | |

TABLE 2-continued

Second paste of paste materials used in Examples and Comparative Examples (parts by weight)

| | | | | | | | | | | | | |
|---|---|---|---|---|---|---|---|---|---|---|---|---|
| Others | Aerosil R972 | 3 | | 3 | | | | | | | | |
| | Aerosil #200 | | 5 | | 5 | 5 | 5 | 5 | 5 | 5 | 5 | 5 |
| | 2AM | | | | | | | | | | | |
| | HEAA | | | | | | | | | | | |
| | BHT | 0.1 | 0.1 | 0.1 | 0.1 | 0.1 | 0.1 | 0.1 | 0.1 | 0.1 | 0.1 | 0.1 |

| | | | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| (a) | acid-reactive glass powder | CK-Si-1 | | | 30 | | | | | | | | |
| | | CK-Si-2 | | | | | | | | | | | |
| (b) | polymer of acidic group-containing polymerizable monomer | PCA1 | | | 10 | | | | | | | | 20 |
| | | PCA2 | 15 | 15 | | 1 | 12.9 | 20 | 6.9 | 6.9 | 22.9 | 3.8 | |
| (c) | water | Distilled water | 26 | 26 | 17.8 | 60 | 50 | 11 | 11 | 51 | 15.8 | 12 | |
| (d) | hydroxyl group-containing (meth)acrylate-based polymerizable monomer | HEMA | 22.6 | 22.6 | 20.6 | 35 | 12 | | 37 | 37 | 12 | 35 | 25 |
| | | GDMA | 10 | 10 | 10 | 20 | 4 | | 20 | 20 | 4 | 20 | 5 |
| | | Bis-GMA | 1 | 1 | 1 | | | | | | | | 2.6 |
| (e) | tri or more functional (meth)acrylamide-based polymerizable monomer | FAM-301 | | | | | | | | | | | |
| | | FAM-302L | | | | 20 | | 14 | | | 20 | | |
| | | FAM-401 | 10 | 10 | 10 | | 2 | | 5 | 5 | 1 | | 10 |
| | | FAM-402 | | | | | | | 5 | 5 | | | |
| (f) | polymerization initiator | BPO | 0.3 | 0.3 | 0.3 | 0.1 | | 1 | | | | 0.1 | 0.3 |
| | | CHP | | | | | 1 | | | | 1 | | |
| | | KPS | | | | | | | | | | | |
| (g) | acidic group-containing polymerizable monomer | 4-MET | | | 10 | 1 | | 5 | 10 | 10 | | 0.2 | 20 |
| | | 10-MDP | 10 | 10 | | | | | | | | | |
| | | 4-META | | | | | | | | | | | |
| | | 4-AET | | | | | 3 | | | 3 | | | |
| Others | | Aerosil R972 | | | | | | | | | | | |
| | | Aerosil #200 | 5 | 5 | 8 | 5 | 5 | 10 | 5 | 5 | 5 | 5 | 5 |
| | | 2AM | | | | | | | | | | | |
| | | HEAA | | | | | | | | | | | |
| | | BHT | 0.1 | 0.1 | 0.1 | 0.1 | 0.1 | | 0.1 | 0.1 | 0.1 | 0.1 | 0.1 |

| | | | Example 23 | Example 24 | Example 25 | Example 26 | Example 27 | Comparative Example 1 | Comparative Example 2 | Comparative Example 3 | Comparative Example 4 | Comparative Example 5 |
|---|---|---|---|---|---|---|---|---|---|---|---|---|
| (a) | acid-reactive glass powder | CK-Si-1 | | | | | | | | | | |
| | | CK-Si-2 | | | | | | | | | | 10 |
| (b) | polymer of acidic group-containing polymerizable monomer | PCA1 | 20 | 20 | 20 | 20 | | 20 | | | | 20 |
| | | PCA2 | | | | | | | 6.9 | 15 | 20 | |
| (c) | water | Distilled water | 8 | 20 | 20 | 20 | 15 | 20 | 11 | 26 | 30 | 20 |
| (d) | hydroxyl group-containing (meth)acrylate-based polymerizable monomer | HEMA | 25 | 25 | 27 | 25 | 40 | 34.6 | 47 | 22.6 | 19.6 | 15 |
| | | GDMA | 5 | 5 | 3 | 5 | 10 | 10 | 30 | 20 | 5 | 5 |
| | | Bis-GMA | 2.6 | 2.6 | 2.6 | 2.6 | 2.6 | 2 | | 1 | | 2.6 |
| (e) | tri or more functional (meth)acrylamide-based polymerizable monomer | FAM-301 | | | | | | | | | | |
| | | FAM-302L | | | | | | | | | | |
| | | FAM-401 | 10 | 10 | 10 | 10 | 10 | | | | | |
| | | FAM-402 | | | | | | | | | | |
| (f) | polymerization initiator | BPO | 0.3 | 0.3 | 0.3 | 0.3 | 0.3 | 0.3 | | 0.3 | 0.3 | 0.3 |
| | | CHP | | | | | | | | | | |
| | | KPS | | | | | | | | | | |
| (g) | acidic group-containing polymerizable monomer | 4-MET | 24 | 12 | 12 | 12 | 12 | 10 | | | 10 | 12 |
| | | 10-MDP | | | | | | | | 10 | | |
| | | 4-META | | | | | | | | | | |
| | | 4-AET | | | | | | | | | | |
| Others | | Aerosil R972 | | | | | 5 | 3 | | | | |
| | | Aerosil #200 | 5 | 5 | 5 | 5 | | | 5 | 5 | 5 | 5 |
| | | 2AM | | | | | | | | | 5 | |
| | | HEAA | | | | | | | | | 5 | |
| | | BHT | 0.1 | 0.1 | 0.1 | 0.1 | 0.1 | 0.1 | 0.1 | 0.1 | 0.1 | 0.1 |

The two-paste type dental resin-reinforced glass ionomer cement compositions of Examples 1 to 27 and Comparative Examples 1 to 5 were evaluated for surface curability, storage stability, coloring resistance (coloring test), water absorption coefficient of linear expansion, and compression strength. In each evaluation, the first paste and the second paste were mixed at a ratio of 1:1 (weight ratio). In addition, a commercially available dental resin-reinforced glass ionomer cement (RelyX Routing Plus/3M) was similarly evaluated (Comparative Example 6). The test results are shown in Table 3. The evaluation method is as shown below.

<Surface Curability>

A stainless mold (diameter 10 mm×thickness 0.5 mm: disk-shaped) was placed on a glass plate installed in a thermostatic chamber at a temperature of 37° C. and a humidity of 100%, and a mixed product of the two-paste type dental resin-reinforced glass ionomer cement composition shown in Examples or Comparative Examples was filled in the mold. After removing the excess mixed material so that the surface became flat, the mixed product was set by irradiating with light for 10 seconds using a dental polymerization light irradiator (trade name: PEN Bright, manufactured by SHOFU INC.) from a height of 5 mm in a state where the surface is opened to prepare a test specimen. The surface of the test specimen was strongly rubbed with a plastic spatula and the surface condition such as the presence or absence of scratches and the extent of scratches was confirmed. Thereafter, water was dropped on the surface and left for 1 minute, and then the water was wiped off with a non-woven cloth or the like, and the surface condition (cloudiness degree of the surface) was confirmed again. The rating criteria are as follows.
AA: There was no stickiness on the surface of the test specimen, and there was almost no scratches or cloudiness.
A: The surface of the test specimen was not sticky, and there was some scratches and cloudiness in a part.
B: The surface of the test specimen was slightly sticky due to the remaining unpolymerized polymerizable monomer, and there was some scratches and cloudiness was present in a large part.
C: The surface of the test specimen was sticky due to the remaining unpolymerized polymerizable monomer, and there was many scratches and cloudiness was present on the entire surface.

Evaluations AA, A and B were set to withstand clinical use.

<Evaluation of Storage Stability>

The mixability immediately after preparation of the two-paste type dental resin-reinforced glass ionomer cement composition shown in Examples and Comparative Examples was evaluated. The paste materials were stored in a thermostatic chamber at a temperature of 50° C. for 2 months, and then the mixability was evaluated again, and was compared with the mixability immediately after preparation. The evaluation criteria are as follows.
A: Almost no change.
B: The mixability was lowered.
C: Separation or gelation of the paste material occurred, or the mixability remarkably deteriorated.

Evaluations A and B were set to withstand clinical use even after storage.

<Coloring Test>

A stainless steel mold (diameter 10 mm×thickness 1 mm: disk) was placed on a smooth glass plate, and a mixed product of the two-paste type dental resin-reinforced glass ionomer cement composition shown in Examples or Comparative Examples was filled in the mold. The mixed product was set by irradiating with light for 10 seconds using a dental polymerization light irradiator (trade name: PEN Bright, manufactured by SHOFU INC.) and the set product was removed from the mold to prepare a test specimen. Using a colorimeter (CM-5, manufactured by Konica Minolta, Inc.), the L*, a*, b* values in the L*a*b* color space on a white plate were measured with SCI method, light source D65, viewing angle 2°. After the measurement, the test specimen was immersed in 5 mL of 37° C. rhodamine solution (0.1%) for 24 hours, then washed with water and dried. After removing the side surface of the test specimen (the side surface of the disk (unpolymerized layer)) with #600 polishing paper, L*, a*, and b* values were measured again, and the color difference before and after immersion in the rhodamine solution was calculated by the following formula. Three test specimens were measured for each sample, and the average value was obtained.

$$\Delta E = ((L^*_1 - L^*_2)^2 + (a^*_1 - a^*_2)^2 + (b^*_1 - b^*_2)^2)^{1/2}$$

The parameters shown in the right side of the formula are as follows.
$L^*_1$: L* value before coloring
$L^*_2$: L* value after coloring
$a^*_1$: a* value before coloring
$a^*_2$: a* value after coloring
$b^*_1$: b* value before coloring
$b^*_2$: b* value after coloring
The criteria for the "coloring test" shown in the table are as follows.
A: ΔE is 0 to less than 40: the test specimen was not colored or slightly colored.
B: ΔE is 40 to less than 50: some coloring were observed in the test specimen.
C: ΔE is 50 or more: the test specimen was markedly colored.

Evaluations A and B were set to withstand long-term clinical use even after storage. In case of 50 or more, it was in a state where the harmony with the natural tooth is not completely obtained.

<Water Absorption Coefficient of Linear Expansion>

A separable stainless steel mold (diameter 4 mm×height 6 mm: columnar) was placed on a smooth glass plate, and a mixed product of the two-paste type dental resin-reinforced glass ionomer cement composition shown in Examples or Comparative Examples was filled in the mold. After pressing the upper surface of the filled mixed product with a smooth glass plate, the mixed product was set by irradiating with light for 10 seconds using a dental polymerization light irradiator (trade name: PEN Bright, manufactured by SHOFU INC.). The set product was allowed to stand for 1 hour in a thermo-hygrostat at 37° C. and −100% relative humidity and was taken out from the mold and used as a test specimen. The length of the test specimen in the axial direction was measured with a micrometer (manufactured by Mitutoyo Corporation) and used as the initial value. After the test specimen was immersed in distilled water at 37° C. for 24 hours after the completion of the mixing, the length in the axial direction was measured in the same manner and used as the test value. Using the obtained values, the water absorption coefficient of linear expansion was calculated by the following formula. Three test specimens were measured for each sample, and the average value was obtained.

Water absorption coefficient of linear expansion
(%)=(test value−initial value)×100/initial value <Compressive Strength Test>

A separable stainless steel mold (diameter 4 mm×height 6 mm: columnar) was placed on a smooth glass plate, and a mixed product of the two-paste type dental resin-reinforced glass ionomer cement composition shown in Examples or Comparative Examples was filled in the mold. After pressing the upper surface of the filled mixed product with a smooth glass plate, the mixed product was set by irradiating with light for 10 seconds using a dental polymerization light irradiator (trade name: PEN Bright, manufactured by SHOFU INC.). The set product was allowed to stand for 1 hour in a thermo-hygrostat at 37° C. and −100% relative humidity, was taken out from the mold and was immersed in distilled water at 37° C. for 24 hours after the completion of the mixing to prepare a test specimen. According to JIST66009-1 (IS09917-1), the compressive strength (MPa) was measured by using an Instron universal tester (Instron 5567A manufactured by Instron Japan) with applying a load in the axial direction of the cylindrical test specimen at a crosshead speed of 1.0 mm/min. Five test specimens were measured for each sample, and the average value was obtained.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty.

Accordingly, any such changes and modifications are intended to be included in the scope of the embodiments.

TABLE 3

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Surface curability | A | AA | A | A | B | AA | AA | AA | A | AA | AA |
| Storage stability | B | A | B | B | B | A | A | A | B | B | A |
| Coloring test (ΔE) | B | A | A | B | B | A | A | A | A | A | A |
|  | 43 | 21 | 38 | 41 | 48 | 29 | 24 | 21 | 27 | 21 | 29 |
| Water absorption coefficient of linear expansion (%) | 1.32 | 1.11 | 1.27 | 1.29 | 1.33 | 1.14 | 1.26 | 1.27 | 1.37 | 1.19 | 1.16 |
| Compressive strength (Mpa) | 123 | 175 | 163 | 131 | 169 | 158 | 163 | 162 | 130 | 145 | 150 |

|  | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|
| Surface curability | A | B | A | A | B | B | B | B | B | AA | AA |
| Storage stability | B | B | B | A | A | A | B | B | B | B | B |
| Coloring test (ΔE) | A | B | A | A | B | B | B | B | B | A | A |
|  | 35 | 40 | 18 | 25 | 47 | 43 | 46 | 47 | 49 | 29 | 33 |
| Water absorption coefficient of linear expansion (%) | 1.55 | 1.75 | 0.86 | 1.11 | 1.4 | 1.32 | 1.65 | 1.75 | 1.69 | 1.18 | 1.19 |
| Compressive strength (Mpa) | 90 | 78 | 180 | 140 | 70 | 101 | 121 | 108 | 118 | 156 | 163 |

|  | Example 23 | Example 24 | Example 25 | Example 26 | Example 27 | Comparative Example 1 | Comparative Example 2 | Comparative Example 3 | Comparative Example 4 | Comparative Example 5 | Comparative Example 6 |
|---|---|---|---|---|---|---|---|---|---|---|---|
| Surface curability | AA | B | B | A | AA | B | B | B | C | Gelation | B |
| Storage stability | B | B | B | A | B | C | C | C | B | — | B |
| Coloring test (ΔE) | A | B | B | A | A | C | B | C | C | — | C |
|  | 33 | 45 | 50 | 33 | 25 | 56 | 49 | 59 | 63 | — | 61 |
| Water absorption coefficient of linear expansion (%) | 1.16 | 1.86 | 1.91 | 1.44 | 1.22 | 1.75 | 1.45 | 1.61 | 1.58 | — | 1.59 |
| Compressive strength (Mpa) | 165 | 113 | 107 | 140 | 169 | 122 | 147 | 119 | 80 | — | 94 |

As shown in Table 3, the two-paste type dental resin-reinforced glass ionomer cement compositions of Examples 1 to 27 were excellent in surface curability and showed high compressive strength. Further, the set product was less colored and had a low water absorption coefficient of linear expansion. Furthermore, the paste materials maintained the mixiability of immediately after preparation even after storage at 50° C. for 2 months. On the other hand, the two-paste type dental resin-reinforced glass ionomer cement compositions of Comparative Examples 1 to 5 and the commercially available dental resin-reinforced glass ionomer cement composition (Comparative Example 6) were poor in any of the properties such as surface curability, compression strength, coloring resistance, water absorption coefficient of linear expansion, and storage stability compared with the two-paste type dental resin-reinforced glass ionomer cement composition of the Examples 1 to 27.

INDUSTRIAL APPLICABILITY

The two-paste type dental resin-reinforced glass ionomer cement composition of the present invention can be used for filling and restoring a tooth in which a form was partially lost by caries breakages and the like and for luting a dental prosthesis device to a tooth in which a form was lost.

What is claimed is:

1. A two-paste type dental resin-reinforced glass ionomer cement composition comprising two pastes, wherein
at least one of the two pastes contains (a) acid-reactive glass powder, (b) polymer of acidic group-containing polymerizable monomer, (c) water, (d) hydroxyl group-containing (meth)acrylate-based polymerizable monomer, (e) tri or more functional (meth)acrylamide-based polymerizable monomer, and (f) polymerization initiator, the paste containing the (c) water does not contain at least one of the (a) acid-reactive glass powder and the (b) polymer of acidic group-containing polymerizable monomer, and the (d) hydroxyl group-containing (meth)acrylate-based polymerizable monomer contains both a mono functional (meth)acrylate-based polymerization monomer that has a hydroxyl group and a bi to tetra functional (meth)acrylate-based polymerizable monomer that has hydroxyl group, and a compounding ratio of the mono functional (meth)acrylate-based polymerization monomer that has a hydroxyl group and the bi to tetra functional (meth)acrylate-based polymerizable monomer that has hydroxyl group is 1:2 to 4:1 by weight.

2. The two-paste type dental resin-reinforced glass ionomer cement composition of claim 1, wherein
at least one of the two pastes further contains (g) acidic group-containing polymerizable monomer, wherein
the paste containing the (c) water does not contain at least one of the (a) acid-reactive glass powder and the (g) acidic group-containing polymerizable monomer.

3. The two-paste type dental resin-reinforced glass ionomer cement composition of claim 1, wherein
the (b) polymer of acidic group-containing polymerizable monomer is a polymer of an α,β-unsaturated carboxylic acid.

4. The two-paste type dental resin-reinforced glass ionomer cement composition of claim 1, wherein
the (e) tri or more functional (meth)acrylamide-based polymerizable monomer is a tetra or more functional (meth)acrylamide-based polymerizable monomer.

5. The two-paste type dental resin-reinforced glass ionomer cement composition of claim 1, wherein
the (e) tri or more functional (meth)acrylamide-based polymerizable monomer is a compound represented by formula (1):

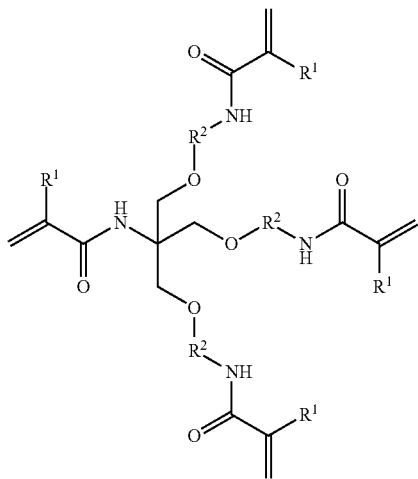

(1)

wherein $R^1$ represents a hydrogen atom or a methyl group and $R^1$s may be the same or different from each other, and $R^2$ represents a linear or branched alkylene group having 2 to 6 carbon atoms which may have a substituent and $R^2$s may be the same or different from each other.

6. The two-paste type dental resin-reinforced glass ionomer cement composition of claim 5, wherein
all $R^1$s in the formula (1) are hydrogen atom.

7. The two-paste type dental resin-reinforced glass ionomer cement composition of claim 1, wherein
the (e) tri or more functional (meth)acrylamide-based polymerizable monomer is a compound represented by formula (2):

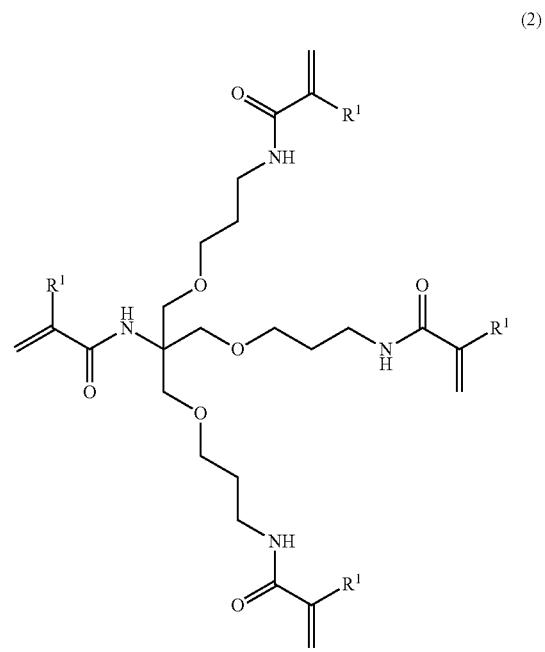

(2)

wherein $R^1$ represents a hydrogen atom or a methyl group and $R^1$s may be the same or different from each other.

8. The two-paste type dental resin-reinforced glass ionomer cement composition of claim 7, wherein
all $R^1$s in the formula (2) are hydrogen atom.

9. The two-paste type dental resin-reinforced glass ionomer cement composition of claim 2, wherein
the (b) polymer of acidic group-containing polymerizable monomer is a polymer of an α,β-unsaturated carboxylic acid.

10. The two-paste type dental resin-reinforced glass ionomer cement composition of claim 9, wherein
the (e) tri or more functional (meth)acrylamide-based polymerizable monomer is a tetra or more functional (meth)acrylamide-based polymerizable monomer.

11. The two-paste type dental resin-reinforced glass ionomer cement composition of claim 10, wherein
the (e) tri or more functional (meth)acrylamide-based polymerizable monomer is a compound represented by formula (1):

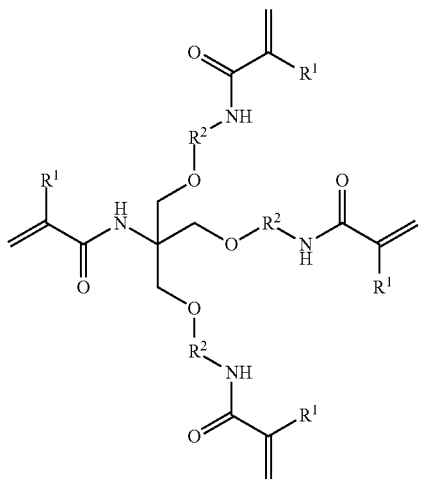

(1)

wherein $R^1$ represents a hydrogen atom or a methyl group and $R^1$s may be the same or different from each other, and $R^2$ represents a linear or branched alkylene group having 2 to 6 carbon atoms which may have a substituent and $R^2$s may be the same or different from each other.

12. The two-paste type dental resin-reinforced glass ionomer cement composition of claim 11, wherein
all $R^1$s in the formula (1) are hydrogen atom.

13. The two-paste type dental resin-reinforced glass ionomer cement composition of claim 10, wherein
the (e) tri or more functional (meth)acrylamide-based polymerizable monomer is a compound represented by formula (2):

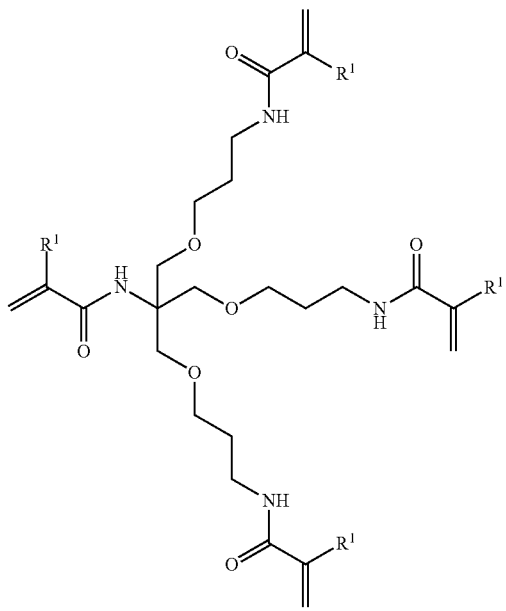

(2)

wherein $R^1$ represents a hydrogen atom or a methyl group and $R^1$s may be the same or different from each other.

14. The two-paste type dental resin-reinforced glass ionomer cement composition of claim 13, wherein
all $R^1$s in the formula (2) are hydrogen atom.

* * * * *